(12) United States Patent
Bashan et al.

(10) Patent No.: US 11,129,556 B2
(45) Date of Patent: Sep. 28, 2021

(54) DEVICE, SYSTEM AND METHOD FOR NON-INVASIVE MONITORING OF PHYSIOLOGICAL MEASUREMENTS

(71) Applicant: WEAR2B LTD., Rosh Pina (IL)

(72) Inventors: Ohad Bashan, Sde Varburg (IL); Oded Bashan, Rosh Pina (IL); Aharon Klein, Haifa (IL); Ben Zion Dekel, Hadera (IL)

(73) Assignee: WEAR2B LTD., Rosh Pina (IL)

( * ) Notice: Subject to any disclaimer, the term of this patent is extended or adjusted under 35 U.S.C. 154(b) by 199 days.

(21) Appl. No.: 16/065,817

(22) PCT Filed: Dec. 28, 2016

(86) PCT No.: PCT/IL2016/051386
§ 371 (c)(1),
(2) Date: Jun. 25, 2018

(87) PCT Pub. No.: WO2017/115361
PCT Pub. Date: Jul. 6, 2017

(65) Prior Publication Data
US 2019/0008432 A1    Jan. 10, 2019

Related U.S. Application Data

(60) Provisional application No. 62/273,517, filed on Dec. 31, 2015, provisional application No. 62/349,681, (Continued)

(51) Int. Cl.
*A61B 5/1455* (2006.01)
*A61B 5/00* (2006.01)
(Continued)

(52) U.S. Cl.
CPC ........ *A61B 5/14558* (2013.01); *A61B 5/0002* (2013.01); *A61B 5/0075* (2013.01);
(Continued)

(58) Field of Classification Search
None
See application file for complete search history.

(56) References Cited

U.S. PATENT DOCUMENTS 4,805,623 A    2/1989    Jobsis
5,086,229 A    2/1992    Rosenthal et al.
(Continued)

FOREIGN PATENT DOCUMENTS

CN    102058400 A    5/2011
CN    103906468 A    7/2014
(Continued)

OTHER PUBLICATIONS

CN Office Action from corresponding CN Appl No. 2016800817753, dated Aug. 5, 2020.
(Continued)

*Primary Examiner* — Eric F Winakur
*Assistant Examiner* — Marjan Fardanesh
(74) *Attorney, Agent, or Firm* — Pearl Cohen Zedek Latzer Baratz LLP

(57) ABSTRACT

System and method for non-invasive monitoring of physiological measurements of a subject, including at least one monitoring device, to detect changes in measured physiological signals, the monitoring device including at least one measuring unit, wherein each measuring unit includes: at least two light emitting sources, and at least one sensor, to detect light beams emitted from the at least two light emitting source, and a computerized device, in communication with the at least one monitoring device, the computerized device to receive data from monitoring device, wherein the monitoring device is configured to be removably attachable to the subject's body.

29 Claims, 12 Drawing Sheets

Related U.S. Application Data filed on Jun. 14, 2016, provisional application No. 62/372,341, filed on Aug. 16, 2016.

(51) Int. Cl.
- *A61B 8/08* (2006.01)
- *A61B 5/107* (2006.01)
- *A61B 5/145* (2006.01)

(52) U.S. Cl.
CPC .......... *A61B 5/14551* (2013.01); *A61B 5/489* (2013.01); *A61B 5/684* (2013.01); *A61B 5/6843* (2013.01); *A61B 5/746* (2013.01); *A61B 8/0858* (2013.01); *A61B 5/1075* (2013.01); *A61B 5/14532* (2013.01); *A61B 5/14546* (2013.01); *A61B 5/441* (2013.01); *A61B 2560/0223* (2013.01); *A61B 2562/0204* (2013.01); *A61B 2562/0238* (2013.01); *A61B 2562/0247* (2013.01); *A61B 2562/043* (2013.01)

(56) References Cited

U.S. PATENT DOCUMENTS

| | | | |
|---|---|---|---|
| 5,188,108 A | 2/1993 | Secker | |
| 5,348,003 A | 9/1994 | Caro | |
| 5,355,880 A | 10/1994 | Thomas et al. | |
| 5,524,617 A | 6/1996 | Mannheimer | |
| 5,823,966 A | 10/1998 | Buchert | |
| 5,974,337 A | 10/1999 | Kaffka et al. | |
| 6,289,230 B1 | 9/2001 | Chaiken et al. | |
| 6,512,937 B2 * | 1/2003 | Blank | A61B 5/14532 128/920 |
| 6,526,297 B1 | 2/2003 | Merilainen | |
| 6,662,031 B1 | 12/2003 | Khalil et al. | |
| 8,022,366 B2 | 9/2011 | Hartley | |
| 8,073,518 B2 | 12/2011 | Chin | |
| 8,100,834 B2 | 1/2012 | Shuler | |
| 8,452,356 B2 | 5/2013 | Vestel et al. | |
| 8,750,952 B2 | 6/2014 | Aalders | |
| 2003/0139681 A1 | 7/2003 | Meiker et al. | |
| 2004/0230107 A1 | 11/2004 | Asada et al. | |
| 2006/0122475 A1 | 6/2006 | Balberg et al. | |
| 2006/0200012 A1 | 9/2006 | Mansour et al. | |
| 2007/0276211 A1 | 11/2007 | Mir et al. | |
| 2008/0146906 A1 | 6/2008 | Baker et al. | |
| 2008/0183388 A1 | 7/2008 | Goodrich | |
| 2009/0022771 A1 | 1/2009 | Lynn et al. | |
| 2010/0056928 A1 | 3/2010 | Zuzak et al. | |
| 2010/0081903 A1 | 4/2010 | Izzetoglu | |
| 2011/0118575 A1 | 5/2011 | Lloyd et al. | |
| 2012/0010477 A1 | 1/2012 | Amano et al. | |
| 2012/0277612 A1 | 11/2012 | Li | |
| 2013/0030267 A1 | 1/2013 | Lisogurski et al. | |
| 2013/0144136 A1 | 6/2013 | Rymut | |
| 2014/0046152 A1 * | 2/2014 | Bechtel | A61B 5/14552 600/323 |
| 2014/0200423 A1 | 7/2014 | Eisen et al. | |
| 2014/0288390 A1 | 9/2014 | Hong et al. | |
| 2014/0350365 A1 | 11/2014 | Sato | |
| 2015/0051498 A1 | 2/2015 | Darty | |
| 2015/0157246 A1 | 6/2015 | Leszinske | |
| 2016/0051147 A1 | 2/2016 | Cohen et al. | |

FOREIGN PATENT DOCUMENTS

| | | |
|---|---|---|
| CN | 103987316 A | 8/2014 |
| JP | H7-508426 | 10/1992 |
| JP | 2007-135621 | 6/2007 |
| JP | 2008-054890 | 3/2008 |
| JP | 2010207274 | 9/2010 |
| JP | 2013-126509 | 6/2013 |
| WO | WO 2008/039299 | 4/2008 |
| WO | WO 2013/160780 | 10/2013 |
| WO | WO 2014/034285 | 3/2014 |
| WO | WO 2014/105520 | 7/2014 |
| WO | WO 2014/165049 | 10/2014 |
| WO | WO 2014/165049 A1 | 10/2014 |
| WO | WO 2015/167251 | 11/2015 |
| WO | WO 2015/176955 | 11/2015 |
| WO | WO 2016/069788 | 5/2016 |

OTHER PUBLICATIONS

Notice of Allowance of U.S. Appl. No. 15/644,855, dated Feb. 19, 2020.

International Search Report of Application No. PCT/IL2016/051386 dated Apr. 4, 2017.

PCT International Search Report and Written Opinion from corresponding PCT Appl No. PCT/IL2018/050748, dated Dec. 13, 2018.

Office Action from corresponding U.S. Appl. No. 15/627,470, dated May 14, 2019.

Office Action from corresponding U.S. Appl. No. 15/644,855, dated Jun. 12, 2019.

Office Action for JP Application No. 2018-534914, dated Nov. 10, 2020.

Australian Office Action for Application No. 2016381563, dated Feb. 4, 2021.

Chinese Office Action for Application No. 201680081775.3, dated Mar. 1, 2021.

Office Action for Japanese Application No. 2018-534914 dated Jun. 22, 2021.

* cited by examiner

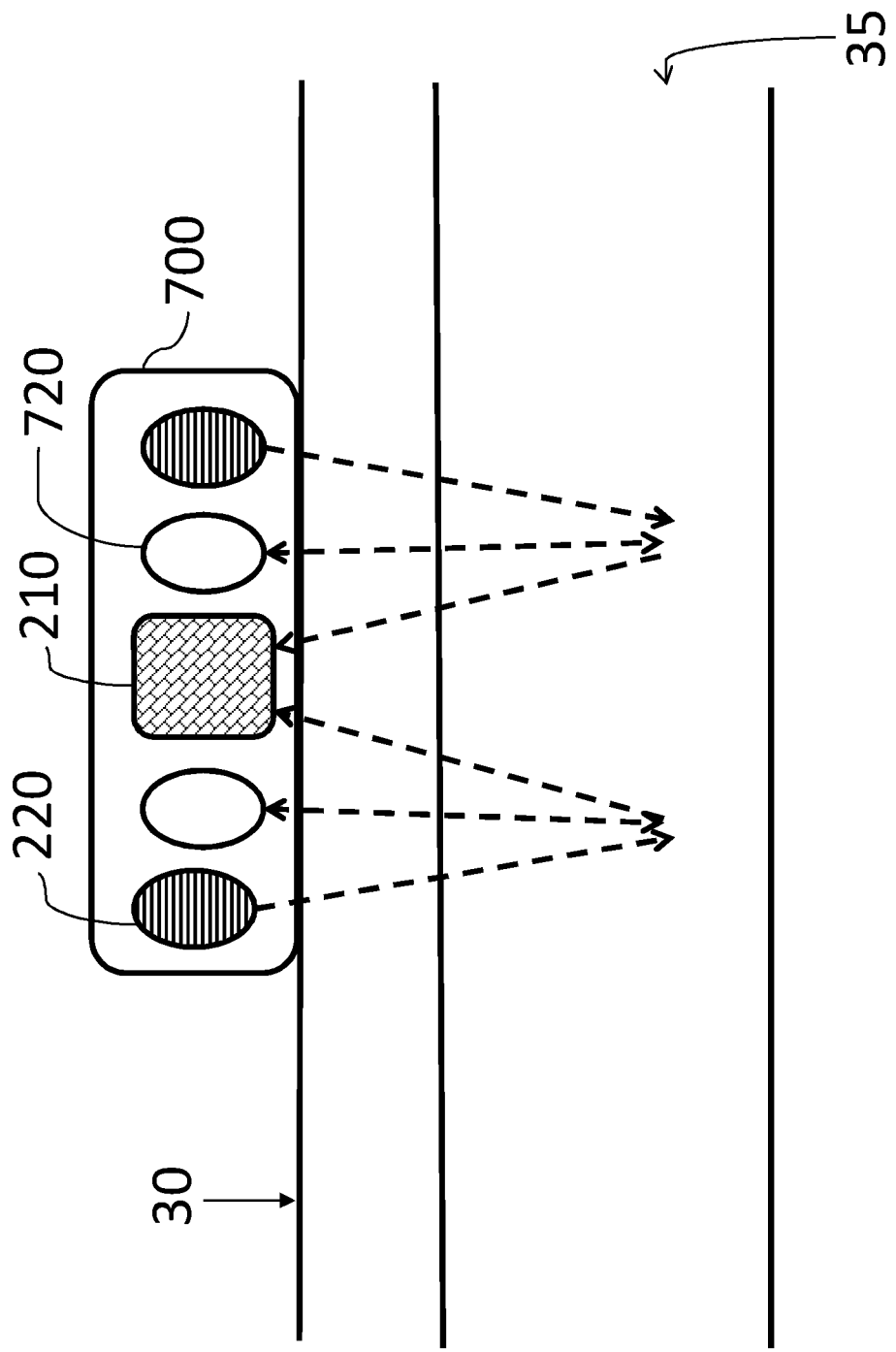

DEVICE, SYSTEM AND METHOD FOR NON-INVASIVE MONITORING OF PHYSIOLOGICAL MEASUREMENTS

CROSS-REFERENCE TO RELATED APPLICATIONS

This application is a National Phase Application of PCT International Application No. PCT/IL2016/051386, International Filing Date Dec. 28, 2016, claiming the benefit of US Provisional Patent Applications Nos. 62/273,517, filed Dec. 31, 2015, 62/349,681, filed Jun. 14, 2016 and 62/372,341, filed Aug. 9, 2016, which are hereby incorporated by reference.

FIELD OF THE INVENTION

The present invention relates to non-invasive physiological measurements. More particularly, the present invention relates to wearable devices, systems and methods for non-invasive monitoring and analyzing of physiological measurements.

BACKGROUND OF THE INVENTION

Many people periodically undergo physical checks in order to monitor any change in their health. For instance taking periodic (e.g., monthly, quarterly) blood tests to check cholesterol levels in the blood, or daily glucose tests with a dedicated device (typically requiring skin puncturing) so as to monitor the glucose levels in the blood.

Since all of these tests are invasive and sometimes painful to the patient, a need arises for a non-invasive solution that could allow users to continuously monitor their physiological characteristics as well as identify trends and changes in the levels of the measured parameters in the blood. Some commercially available products allow non-invasive measurements of physiological signs such as pulse or temperature, however these solutions are not very accurate and there is no available solution to replace the current invasive measurements, capable of measuring blood components levels in a non-invasive manner.

SUMMARY OF THE INVENTION

There is thus provided, in accordance with some embodiments of the invention, a monitoring device adapted to be removably attachable to a subject's body, the device including a measuring unit with at least two light emitting sources, at least one sensor, to detect light beams emitted from the at least two light emitting source, and a controller, coupled to the measuring unit, and configured to measure and analyze physiological signs of the subject. In some embodiments, the monitoring device may be wearable.

In some embodiments, a first sampling frequency may be used for a first measured physiological characteristic, and a second sampling frequency may be used for a second measured physiological characteristic. In some embodiments, the at least one sensor may be a light sensor configured to detect light beams emitted from the at least one light emitting source that are reflected from a subcutaneous tissue of the subject.

In some embodiments, at least one light emitting source of the at least two light emitting sources, may operate at a different wavelength than at least another light emitting source of the at least two light emitting sources. In some embodiments, the number of different wavelengths may be determined based on the substance to be measured. In some embodiments, light beams may be emitted from each light emitting source in predetermined time intervals.

In some embodiments, at least one light emitting source may be a polarized light source configured to emit light beams with a predetermined polarization, and wherein at least one sensor may be a polarized light sensor configured to detect reflection of the polarized light beams, wherein the polarized sensor has a different polarization than the polarized light source.

In some embodiments, the device may further include a communication module, configured to allow communication with external computerized devices. In some embodiments, the device may further include a power storage unit.

In some embodiments, the communication module may be configured to allow wireless communication. In some embodiments, the device may further include a memory module configured to store measurement data to be sent to an external computerized device. In some embodiments, the device may further include a pressure sensor to indicate excessive pressure on the skin of the subject.

There is thus provided, in accordance with some embodiments of the invention, a system for non-invasive monitoring of physiological measurements of a subject, the system including at least one monitoring device, to detect changes in measured physiological signals, the monitoring device comprising at least one measuring unit, wherein each measuring unit includes at least two light emitting sources, at least one sensor, to detect light beams emitted from the at least two light emitting source, and a computerized device, in communication with the at least one monitoring device, the computerized device to receive data from monitoring device. In some embodiments, the monitoring device may be configured to be removably attachable to the subject's body.

In some embodiments, the communication between the monitoring device and the computerized device may be wireless. In some embodiments, at least one light emitting source of the at least two light emitting sources may operate at a different wavelength than at least another light emitting source of the at least two light emitting sources.

In some embodiments, the number of different wavelengths may be determined based on the substance to be measured. In some embodiments, a first wavelength and/or frequency may be used for a first measured physiological characteristic, and a second frequency may be used for a second measured physiological characteristic.

In some embodiments, the measurement wavelength and/or frequency may correspond to changes in measured physiological signals. In some embodiments, the computerized device may be selected from a group consisting of a mobile phone, a tablet, a personal computer, and a mobile computer. In some embodiments, data may be transferred between the monitoring device and the computerized device via a communication module. In some embodiments, data may be transferred wirelessly. In some embodiments, data may be transferred between the monitoring device and the computerized device in predetermined time intervals.

In some embodiments, the computerized device may include a display with a user interface. In some embodiments, the measuring unit may further include an ultrasound unit configured to determine skin tissue thickness. In some embodiments, the system may further include a data analyzing facility, in communication with the computerized device, the data analyzing facility to analyze measured physiological signals for at least one subject.

In some embodiments, the ultrasound unit may be further configured to determine array proximity to blood vessels under the skin of the subject. In some embodiments, the system may further include an acoustic sensor to provide acoustic data to the computerized device to be combined with optical data from the light emitting sources.

In some embodiments, the system may include at least one sensor to detect light reflected from the skin of the subject, and at least one sensor to detect light transmitted through the skin of the subject.

There is thus provided, in accordance with some embodiments of the invention, a method of non-invasive monitoring of physiological measurements of a subject, the method including emitting light beams towards the skin of the subject, with at least two light sources, sampling the physiological signals of the subject, with at least one light sensor, based on detected reflected light beams, and issuing an alert upon detection of a change in measured physiological signals exceeding a predetermined threshold.

In some embodiments, sampling the physiological signals of the subject may be carried out repetitively every predefined time period. In some embodiments, a first frequency may be used for a first measured physiological characteristic, and a second frequency may be used for a second measured physiological characteristic. In some embodiments, the method may further include comparing two consecutive measurements to detect a change.

In some embodiments, the method may further include calibrating intensities of light sources emitting light to be reflected from a known blood vessel and detected thereon. In some embodiments, the method may further include receiving an indication on position on the skin of the subject that is proximal to a blood vessel. In some embodiments, the indication may be received upon measurement of a pulse signal.

In some embodiments, the method may further include comparing data of emitted light beam and detected light beam, and providing an indication on radiation absorption by the blood based on the comparison. In some embodiments, the method may further include directing each emitted light beam in a predefined direction. In some embodiments, the method may further include adjusting the light source to be aligned with an adjacent blood vessel.

In some embodiments, the method may further include adjusting the wavelength of at least one emitted light beam. In some embodiments, the sampling may be initiated upon detection of contact with the skin of the subject. In some embodiments, the method may further include checking if sampled data is within a predetermined range, and issuing an alert if the sampled data exceeds the predetermined range.

In some embodiments, the method may further include comparing the sampled data to at least one stored data set. In some embodiments, the method may further include checking if the wavelength of the emitted light beams is within a predetermined range. In some embodiments, the method may further include adjusting the wavelength of the emitted light beams. In some embodiments, the method may further include monitoring thickness of skin tissue of the subject. In some embodiments, the method may further include associating each subject to a personal reflectance coefficient, and adjusting the sampled data based on the personal reflectance coefficient.

In some embodiments, the method may further include associating each subject to a personal reflectance coefficient, comparing two consecutive measurements to detect a change, and applying a compensation function for readings with the detected change based on the personal reflectance coefficient.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 7 schematically illustrates a cross-sectional view of a measuring unit with an embedded ultrasonic unit coupled and adjacent to the subject, according to some embodiment of the present invention;

Figure 1:
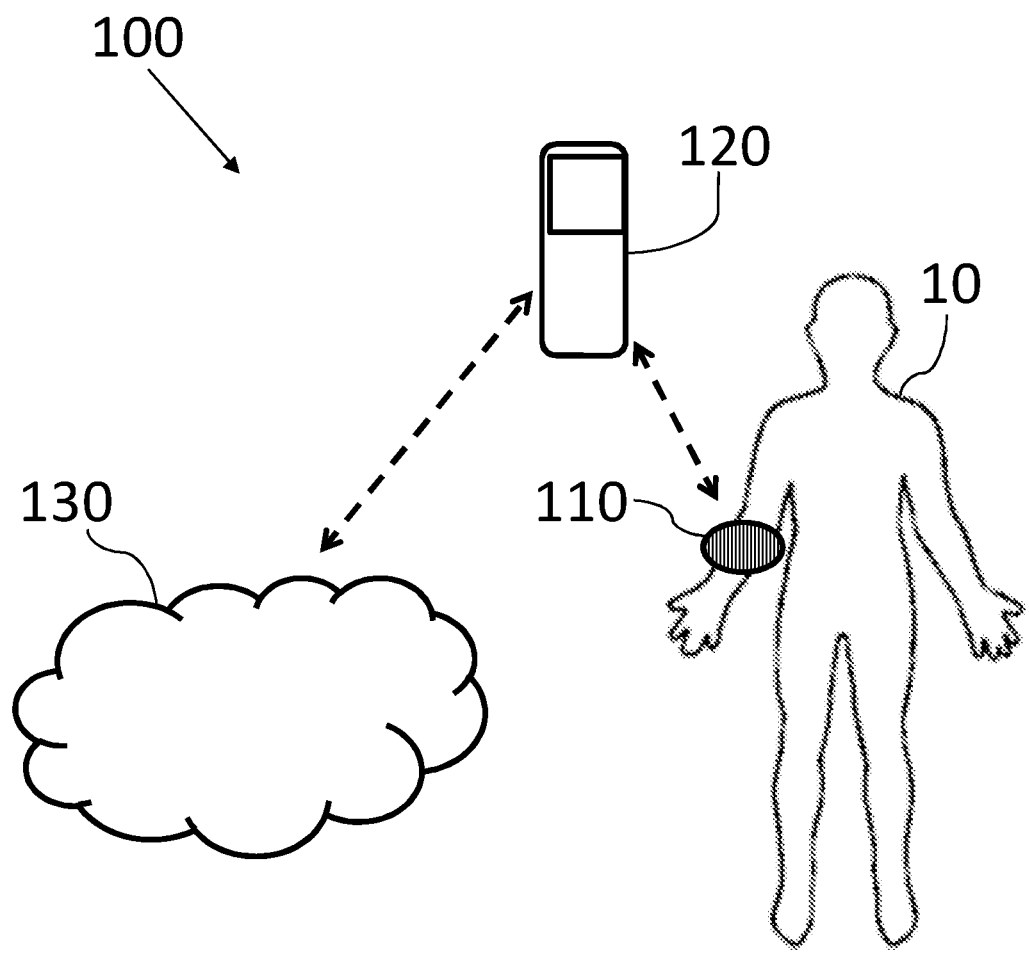
FIG. 1 schematically illustrates a non-invasive monitoring system, according to some embodiments of the present invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the invention may be practiced without these specific details. In other instances, well-known methods, procedures, and components modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g. electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Reference is now made to FIG. 1, which schematically illustrates a non-invasive monitoring system (wherein the direction of dashed arrows may indicate the direction of information flow), generally designated 100, according to some embodiments of the invention. The non-invasive monitoring system 100 is designed to allow continuous and/or repetitive non-invasive monitoring of a subject 10, using a wearable monitoring device 110. The wearable monitoring device 110 may be wearable on a limb of the subject 10, or alternatively on other parts of the body (e.g. on a finger, on the ear, etc.).

It should be appreciated that wearable device 110 may collect continuous data on the physiological signals (e.g., pulse, blood components levels, etc.) of the subject 10, as long as device 110 is worn by the subject 10, and therefore wearable device 110 may provide ongoing data such that changes in measured physiological signals may be detected. In some embodiments, wearable device 110 may collect the data when wearable device 110 is worn by the user, and provide the collected data to user even when device 110 is not worn by the subject 10.

According to some embodiments, wearable device 110 may be configured to sample the physiological signals of subject 10 repetitively every predefined time period. In some embodiments, the frequency of sampling may be equal to or higher than Nyquist rate. When wearable monitoring device 110 is configured to measure non-invasively various physiological characteristics of the subject 10, different frequencies of sampling may be used for each measured physiological characteristic.

According to some embodiments, monitoring system 100 may further include a computerized device 120 (e.g. a processor in the vicinity of subject 10), that is configured to receive data from wearable monitoring device 110 and may allow processing (e.g. with a processor) of the received data thereof. In some embodiments, computerized device 120 may be or may include, for example, a mobile phone, a tablet, a personal computer, a mobile computer, or any other suitable computing device 120. For example, system 100 as described herein may include one or more devices such as computerized device 120.

According to some embodiments, monitored data may be transferred from computerized device 120 to wearable monitoring device 110, and vice versa, via a compatible communication module (e.g. via Wi-Fi, Bluetooth, NFC, etc.). For example, a user 10 wearing wearable monitoring device 110 and also operating a mobile phone, may utilize the mobile phone as computerized device 120 in order to transfer data to and from wearable monitoring device 110 via wired and/or wireless communication.

In some embodiments, wearable monitoring device 110 may include a measuring unit (200 in FIG. 2) with a dedicated controller that may be configured to measure physiological signs of subject 10 (further described with reference to FIGS. 2, 3A and 3B hereinafter), a communication module configured to allow communication with computerized device 120 via, for example, wireless communication, and a power storage unit (e.g. a battery). Computerized device 120 may include compatible components that are configured to allow the data transfer to and from the wearable monitoring device 110, and to allow processing of data received from wearable monitoring device 110. For instance, computerized device 120 may include a compatible communication module, a display (e.g. with a user interface), and a processor capable of processing and monitoring the physiological data of subject 10 measured by monitoring device 110.

Computerized device 120 may have, according to some embodiments, a dedicated user interface (e.g. with a dedicated algorithm installed thereon) so as to display real-time measurements to subject 10. Thus, the user may receive alerts and/or updates regarding the physiological signs that were measured by the wearable monitoring device 110. In some embodiments, computerized device 120 may issue an alert upon detection of a change in measured physiological signals exceeding a predetermined threshold.

In some embodiments, monitoring system 100 may further include a data analyzing facility 130, e.g. such as one or more server computers in communication with one or more wearable devices. The data analyzing facility 130 may include a computerized device with a dedicated database for processing and analyzing measurement data from one or more subjects 10, such as physiological signals, blood parameters (e.g. medication concentration in the blood, blood chemistry etc.) and the like.

Such a data analyzing facility 130 may be adapted to carry out at least one of big data analysis, machine learning, and data mining tasks. Thus, data analyzing facility 130 may analyze physiological signals from multiple subjects and thereby deduce desirable ranges and trends for physiological measurements and medical insights, as further described hereinafter.

In some embodiments, the analyzing and processing of the measured data may be carried out on a dedicated processor embedded into monitoring device 110.

In some embodiments, the dedicated measuring algorithm may provide predetermined time intervals for performing measurements and/or time intervals for sending data from wearable monitoring device 110 to computerized device 120. Furthermore, the measuring algorithm may also provide predetermined time intervals for sending data from computerized device 120 to data analyzing facility 130. In some embodiments, these predetermined time intervals may be altered by the user (e.g., subject 10, a caregiver and the like) and/or by the dedicated measuring algorithm.

For instance, monitoring system 100 may receive data from wearable monitoring device 110 indicating a sharp rise in the glucose level in the blood, so that the dedicated measuring algorithm may automatically increase the frequency and/or duration of the time intervals for performing measurements so as to gather additional information prior to sending an alert to subject 10. In some embodiments, the time intervals between measurements may be reduced, for instance upon receiving data from wearable monitoring device 110 indicating a drop in the glucose level in the blood.

In some embodiments, the monitoring system 100 may perform self-optimization by learning the behavior of the subject 10. For instance, learning specific time periods during the day when the subject 10 engages in sport activity, affecting the expected values of measured physiological signs (e.g. pulse, blood pressure and the like) and storing data for such time periods in a dedicated memory and/or database. With such optimization, monitoring system 100 may only perform measurements that give actual information on the subject in a "relaxed state" (e.g., where the subject does not perform any physical activity), as well as saving electrical power for the wearable monitoring device 110, since redundant measurements are reduced or completely prevented.

In some embodiments, wearable monitoring device 110 may further include a memory module that is configured to store measurement data to be sent at a later time. This feature may allow the system to save electrical power by sending data only at predetermined intervals. In some embodiments, only a predetermined type of data may be stored on this memory module, for instance storing a record of daily glucose level measurements.

Figure 2:
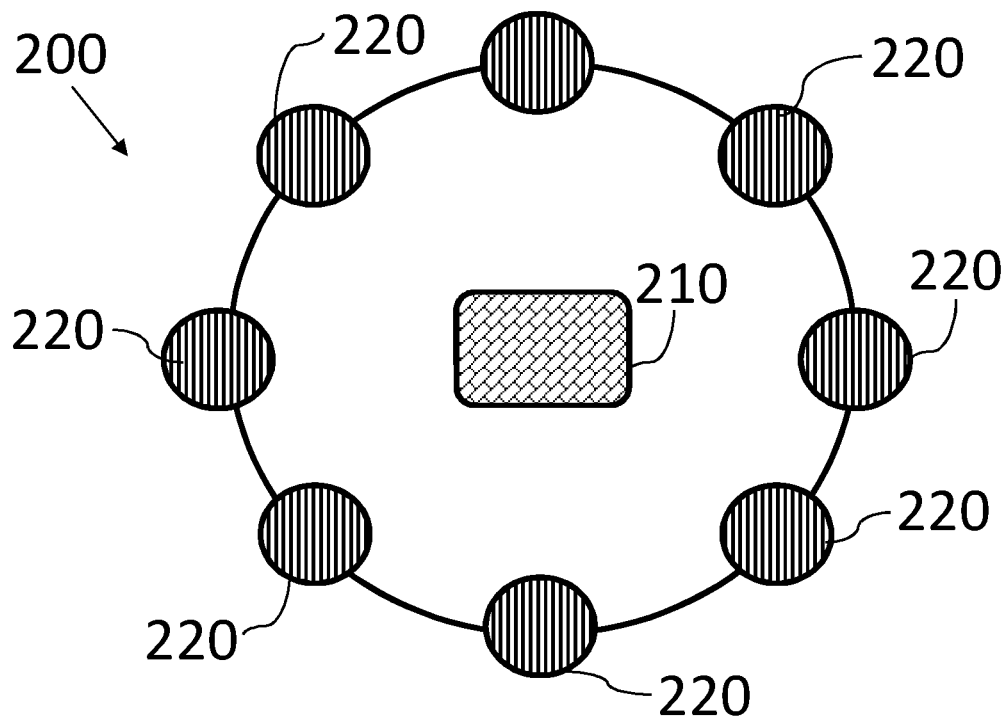
FIG. 2 schematically illustrates a measuring unit for a wearable monitoring device, according to some embodiments of the present invention.

Reference is now made to FIG. 2, which schematically illustrates a measuring unit 200 for a wearable monitoring device, according to some embodiments of the present invention. Measuring unit 200 may include at least one sensor 210 and at least one light emitting source 220. In some embodiments, measuring unit 200 is adjacent to and in contact with the skin of subject 10 so as to reduce noises from the environment. It should be noted that with light beams emitted from the at least one light emitting source 220 towards subject 10, the wearable monitoring device may perform optical measurements (e.g. with at least one sensor 210) that are non-invasive.

In some embodiments, multiple measuring units 200 may be employed (for instance as an array) in order to allow simultaneous monitoring of several blood vessels of the subject 10. For example, an array of three adjacent measuring units 200. In some embodiments, the monitoring system 100 may operate different light emitting sources 220 within the multiple measuring units 200 in order to achieve optimal measurements (for example initiating only sources 220 closest to detected blood vessels). Such an array may allow measurements in parts of the body having different distributions of blood vessels, whereby the monitoring system 100 may choose to operate a particular measuring unit 200 that is closest to a blood vessel. In some embodiments, each measuring unit 200 may be operated in a different wavelength, for instance in order to allow simultaneous measurements of different features (e.g. glucose, insulin, LDL, VLDL and Albumin). In some embodiments, measurements of different substances (e.g. glucose and Albumin) may be carried out with different wavelengths and/or different number of wavelengths. For example, measurements of glucose may require each measuring unit 200 to be operated in eight different wavelengths, while measurements of Albumin may require each measuring unit 200 to be operated in six other wavelengths.

The light emitted from the at least one light emitting source 220 (e.g. LED), to be reflected from a subcutaneous tissue (e.g. from blood in a blood vessel in the subcutaneous tissue) of the subject, and then detected by the at least one sensor 210 may be, according to some embodiments, in the Infra-Red or near Infra-Red (IR) spectrum. In some embodiments, Short Wave IR (SWIR) imaging is utilized for measuring physiological signals from the blood of subject 10. The SWIR waveband runs from the lower edge of the near IR region at 900 nm up to 2500 nm, and may be utilized for inspection of blood and blood components in blood vessels of the subject 10. It should be noted that if required, the range of the SWIR waveband may be increased.

It should be noted that the measuring unit 200 may be provided in various configurations, and in some embodiments a single sensor 210 is surrounded by a plurality of light emitting sources 220 (as for example illustrated in FIG. 2). Other configuration may also employ a plurality of sensors 210 and light emitting sources. For example, a plurality of sensors 210, where each sensor 210 is surrounded by a plurality of light emitting sources 220 and where at least two sensors 210 may share at least one light emitting source 220.

In some embodiment, each light emitting source 220, or sub-sets (e.g. pairs, triplets etc.) of light emitting sources 220 may emit light in a different predetermined wavelength.

In some embodiment, each light emitting source 220, or sub-set of light emitting sources 220, may emit light in a different time and/or in a different frequency, such that not all light emitting sources 220 emit light simultaneously. This may provide additional information on the reflected tissue when the time intervals between the emissions of light beams is known.

According to some embodiments, the frequency of sampling by each light emitting source 220, or by each sub-set of light emitting sources 220, may be equal to or higher than Nyquist rate of the measured physiological signal.

In some embodiments, polarized optical means may be utilized in order to increase the accuracy in the optical measurements. Specifically, emitting light beams with a predetermined polarization and receiving these beams with a substantially different polarization, for instance with dedicated filters, may improve the signal to noise ratio in the measurements. Furthermore, such polarizing may also provide improved indication on the penetration of the light beam into the tissue as noises from the external skin layer may be reduced while only signals from the beam reflected from the blood is measured.

In some embodiments, at least one light emitting source may be a polarized light source configured to emit light beams with at least one predetermined polarization (e.g. in an alternating mode such that at least one emitted light beam is not polarized), and wherein at least one sensor may be a polarized light sensor configured to detect reflection of the polarized light beams, wherein the polarized sensor has a different polarization than the polarized light source.

In some embodiments, other sensors may also be utilized. For example acoustic ultrasound sensors, as well as photoacoustic sensors, terahertz sensors, RF sensors, microwave sensors and corresponding energy sources.

In some embodiments, the light emitting source (e.g. LED) may be operated in pulse width modulation (PWM) mode with a configurable duty cycle. As may be apparent to one of ordinary skill in the art, the pulse width of a duty cycle may be as small as about ~0.01%. In some embodiments, the pulse width may also be changed during measurements by data analyzing facility 130 corresponding to the actual readings.

In addition, in some embodiments, at least one sensor 210 may be synchronized with at least one light emitting source 220 by applying a band pass filter that blocks all information not correlated to the PWM switching frequency. Such a band pass filter may be adjustable to allow frequency change during operation, for example as calculated by analyzing facility 130.

Figure 3A:
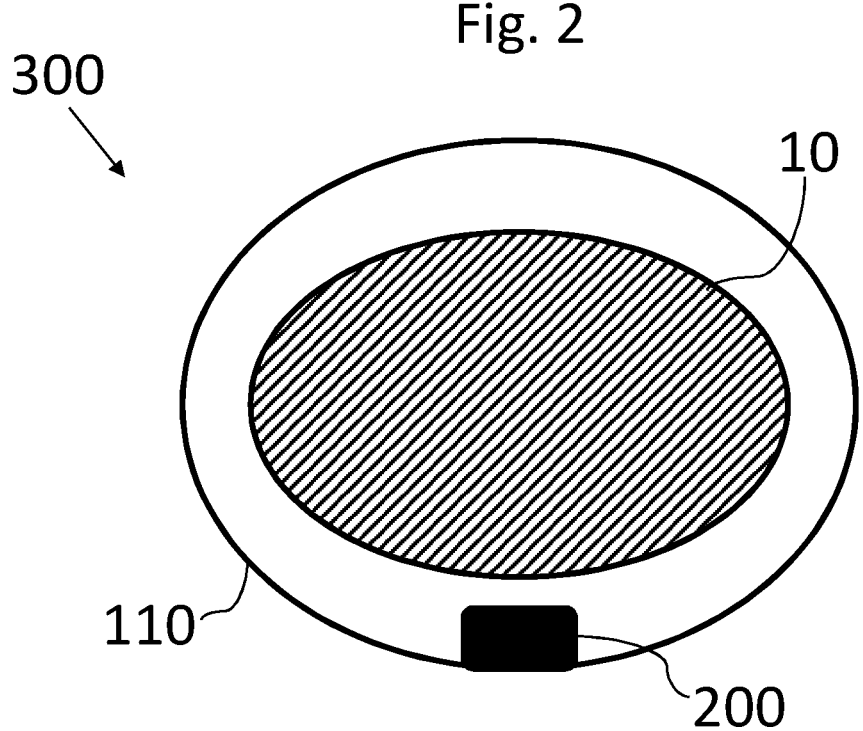
FIG. 3A schematically illustrates a cross-sectional view of the wearable monitoring device with the measuring unit as worn by the subject, according to some embodiments of the present invention.
Figure 3B:
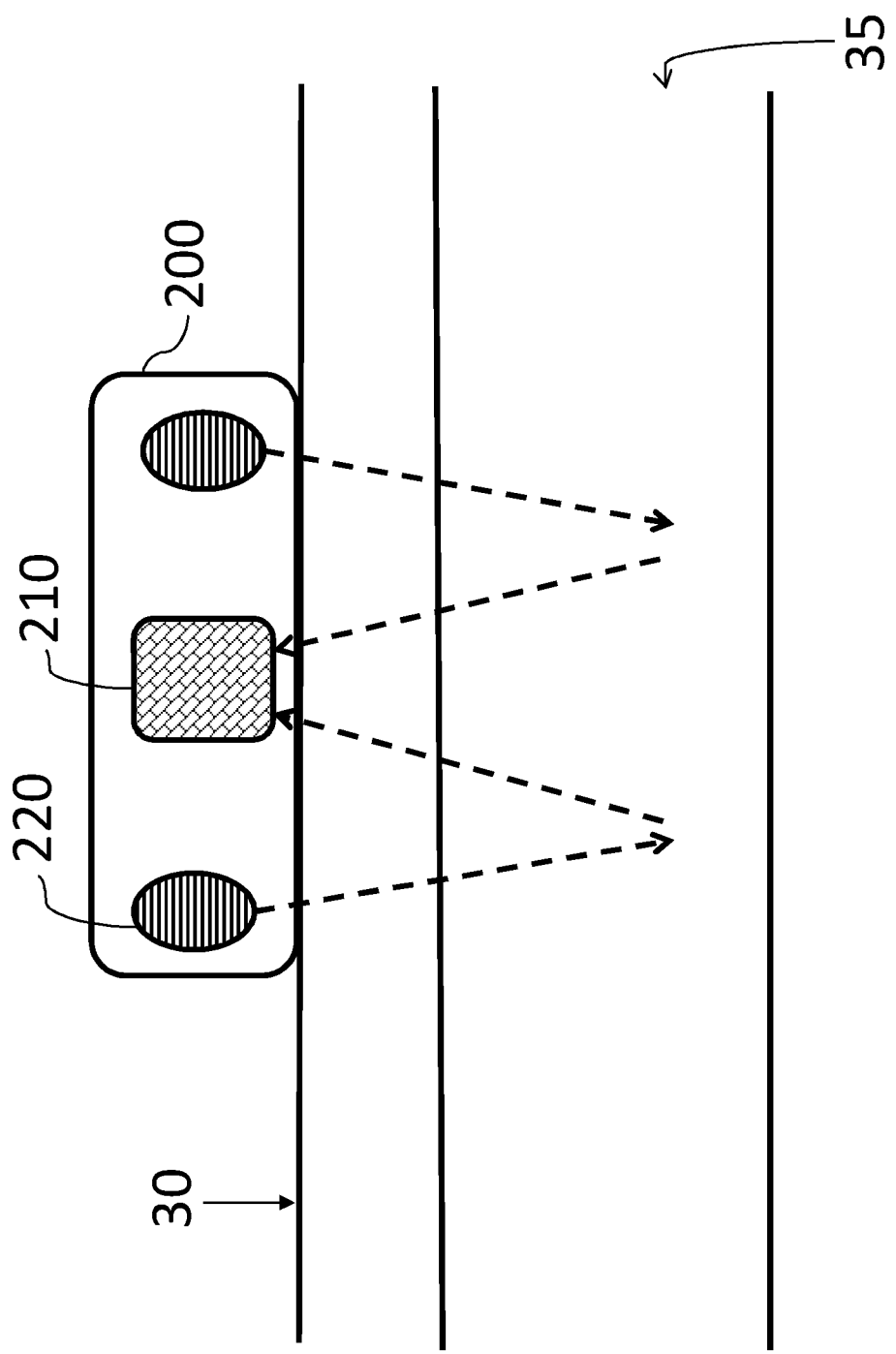
FIG. 3B schematically illustrates a cross-sectional view of the measuring unit coupled and adjacent to the subject, according to some embodiments of the present invention.

Reference is now made to FIGS. 3A-3B, which show wearable monitoring device 110 coupled to the body of the subject 10. FIG. 3A schematically illustrates a cross-sectional view of wearable monitoring device 110 with measuring unit 200 worn on a limb of subject 10, generally designated 300, according to some embodiments of the present invention.

In some embodiments, wearable monitoring device 110 encompasses a portion of the body of the subject 10 (e.g. a finger or the wrist, or leg), wherein the emitted light is reflected back from a blood vessel (e.g. as shown in FIG. 3B). Alternatively, in other embodiments, the wearable monitoring device 110 may be clipped onto a different portion of the body (e.g. the ear), wherein the emitted light passes through that portion and is transmitted to the sensor on the other side of the wearable monitoring device 110. According to some embodiments, at least one wearable monitoring device 110 may simultaneously detect with at least one sensor light reflected back from a blood vessel and/or detect light transmitted through a portion of the body of the subject 10.

For example, measuring unit 200 may be embedded into a band like wearable monitoring device 110, which is worn on the wrist of the subject 10. Thus, the measuring unit 200 may be sufficiently adjacent to the skin to prevent exposure of sensor 210 (in FIG. 2) to ambient light, and to detect light beams (with the sensor 210) emitted from the light emitting source 220 and reflected from blood in a blood vessel.

In some embodiments, the wearable monitoring device 110 may include a bracket that is capable of sensing whether the wearable monitoring device 110 is in an operable state. For example, a bracket that triggers the wearable monitoring device 110 to commence monitoring once appropriate contact with subject 10 is achieved (e.g. once a wrist band is secured onto the wrist of a user).

In some embodiments, multiple wearable monitoring devices 110 may be employed by the same subject 10 in order to provide accurate measurement with comparison to measurements from different parts of the body. For example, a first wearable monitoring device 110 worn on the wrist, and a second wearable monitoring device 110 worn on the leg.

In some embodiments, wearable monitoring device 110 may further include a pressure sensor that is configured to indicate excessive pressure on the skin of the subject 10. This may be performed so as to allow adjustment of wearable monitoring device 110 fastener (e.g. to reduce or increase the pressure), for instance by manipulating the coupling of the wearable monitoring device 110 to the skin (e.g. physically moving the monitoring device 110), in order to adjust the pressure on the skin and thereby reduce noise from the measurements.

It should be noted that in order to receive an accurate measurement, the sensor 210 of the measuring unit 200 should be adjacent to the skin of the subject 10, such that it may measure light signals that are reflected from a blood vessel. In some embodiments, the signal intensity from each light emitting source 220 may indicate the proximity to a blood vessel, based on previously calibrated light sources that were placed over a known blood vessel. Thus, a processor of monitoring system 100 may select only some of the light emitting sources 220 that are proximal to the blood vessel to perform the optical measurements (i.e. emit the light beams). In some embodiments, once the monitoring system 100 receives an indication on a position that is proximal to a blood vessel then the light emitting sources 220 may receive a signal to initiate the measurements.

As may be apparent to one of ordinary skill in the art, light in specific wavelengths between 400-2500 nm (e.g. 417 nm, 545 nm, or 578 nm), reflected from subcutaneous tissue (e.g. reflected from blood inside a blood vessel) and light reflected from tissue above a blood vessel have different intensities since light reflected from tissue above a blood vessel have a weaker reflection due to higher light absorption in water content. Therefore, it may be possible to determine a threshold for determining position of measuring unit 200 being over a blood vessel.

In some embodiments, the monitoring system 100 may further include positioning correction indicators (not shown) that are adapted to allow the user to correctly place measuring unit 200 over a blood vessel. For instance, displaying to the user how to move monitoring device 110 to improve positioning of light emitting sources 220 to optimize reflections to the sensor.

In some embodiments, the measurements of a pulse signal may provide indication that the measuring unit 200 is in a proper position, when a sufficiently strong pulse signal is received. A sufficiently strong pulse signal may refer to a signal above a predefined threshold. In some embodiments, the monitoring system 100 may be utilized for measurement of medication concentration and/or existence of medication in the blood, for instance by monitoring a different range of wavelengths.

According to some embodiments, the wearable monitoring device may be provided as a patch (or sticker) that is removably attached to the skin of the object while having the same features as described above, and capable of monitoring the object. Such a patch-like monitoring device may be particularly helpful to users that wish to perform measurements at various locations on the body, and for instance without wearing a wearable devices on their limbs.

FIG. 3B schematically illustrates a cross-sectional view of the measuring unit 200 coupled and adjacent to the subject 10 (wherein the direction of the dashed arrows indicates the direction of the light beams), according to some embodiments of the present invention.

Measuring unit 200 may be placed adjacent to the skin 30 of subject 10 (in FIG. 1). A light beam may then be emitted (e.g. periodically every 5 minutes, every 10 minutes, or at any other time or frequency) from the light emitting source 220 and into the skin such that it penetrates the skin and may be reflected back from blood vessel 35 towards sensor 210. The difference in the data between the emitted beam and the received (reflected) beam may provide an indication on the radiation (e.g., light) absorption by the blood in blood vessel 35 and thus may indicate characteristics and blood measurements of the blood inside blood vessel 35, in a non-invasive procedure. In some embodiments, each light emitting source 220 may be provided with an optical collimator (or reflector)

so as to allow directing the light beam emitted by each light source 220 in a specific predefined direction.

For example, such measurements may provide an indication for a "health matrix" with continuous glucose monitoring, dehydration monitoring, blood lipids, vitamins, calories, pulse, PWV (Pulse wave velocity) blood pressure, and also an indication of medications, pharmaceuticals and other chemicals in the blood stream of the subject. It is appreciated that in order to provide an alert to the subject regarding for example, glucose measurements, it may be sufficient to indicate a (predetermined minimal) change in the level and/or trend of glucose in the blood, such that a precise and accurate measurement is not always required. Thus, the system may continuously or repetitively monitor the glucose levels and/or glucose trends and indicate upon measuring a change. In some embodiments, the system may perform a continues measurement or multiple measurements only upon indication of a significant change such that power is saved and the system operates in "low energy consumption" mode.

In some embodiments, the orientation of the emitted light beam may be controlled, for instance with dedicated beam controlling elements of angle and position, so as to allow control of the depth of the penetration of the beam that corresponds to the relative angle of emission.

In some embodiments, data analyzing (e.g. by the computerized device) of such non-invasive measurements may provide a prediction regarding at least one of the following: diabetes (e.g., through glucose levels monitoring), dehydration (e.g., through water level, cortisol, blood albumin level, urea level, and skin temperature monitoring), medication compliance (e.g., Depalept, Plavix clopidogrel, cyclosporine Anti-hypertensive drugs, Metformin-Glucophage, Lipitor-Statins, Cannabinoids based drugs, etc.), Creatine kinase, Cardiac troponin, Hs CRP-C reactive protein, Cholesterol LDL/HDL, Triglycerides, and blood lipids such as high-density lipoprotein (HDL), low-density lipoprotein (LDL), and very-low-density lipoprotein (VLDL). In some embodiments, such non-invasive measurements may provide a prediction regarding Cholesterol lowering medications (e.g. Statins, Niatzin, and fibrates) and/or blood pressure lowering medications (e.g. thiazides) and/or diabetes lowering medications (e.g. biguanidins, glitazones, sulfinyl urea, and insulin).

In some embodiments, such measurements may allow issuing alerts before life threatening conditions, such as heart abnormality or stroke, by continuously monitoring and collecting personal data to detect changes for instance in low density lipoprotein (LDL), Albumin, glucose, etc.

In some embodiments, the optical measurements (e.g. light emitting diode (LED)) for glucose may be performed with wavelengths in the range of about ~900 nm-2500 nm. In some embodiments, a glucose measurement may also be performed with acoustic means (e.g. an ultrasound sensor) whereby the sensor may receive a sound (e.g. ultrasound) waves reflected from the blood in the subject's blood vessels. In some embodiments, other or additional substances may be measured within the blood using such acoustic means, and/or medicament concentrations may also be measured using such acoustic means.

In some embodiments, the optical measurements (e.g. LED) for Oxygen saturation may be performed with additional wavelengths of about ~660 nm and/or about ~910 nm with a comparison of oxygenized and deoxygenized hemoglobin.

In some embodiments, the monitoring system may be pre-calibrated prior to initial operation with a specific subject, based on average measurements from multiple users or alternatively calibrated for a specific subject, for instance compared to measurements from other devices (e.g. calibrating glucose measurement's versus a commercially available glucometer).

In some embodiments, the optical measurements (e.g. LED) for lipids and cholesterol may be performed with wavelengths of about ~930 nm, ~1210 nm, ~1400 nm, ~1730 nm and/or ~1760 nm.

In some embodiments, the optical measurements (e.g. LED) for hemoglobin may be performed with additional wavelengths of about ~400 nm, ~815 nm, and/or ~950 nm checking the red cells level in the blood.

In some embodiments, the optical measurements (e.g. LED) for Bilirubin may be performed with wavelengths of about ~460 nm, and/or ~585 nm, and/or ~650 nm checking the Bilirubin level in the blood as well as liver functioning.

It should be appreciated that hematocrit measurements (i.e. percentage of red blood cells volume in total blood volume) may differ between men and women, for instance being 42-52% in men and 36-48% in women. Thus, the values of different parameters in the blood may be adjusted for the specific subject group of the user (e.g. for a female user) since the concentration of a particular substance may be different, thereby providing substantially different values.

In some embodiments, the optical measurements (e.g. LED) for a substantially constant parameter, such as Albumin, total serum proteins, globulins or any combination of thereof, may be performed, checking the constant parameter's level in the blood. In some embodiments, the optical measurements (e.g. LED) for alcohol may be performed with wavelengths of about ~1250-2500 nm checking the Ethanol level in the blood.

Figure 4:
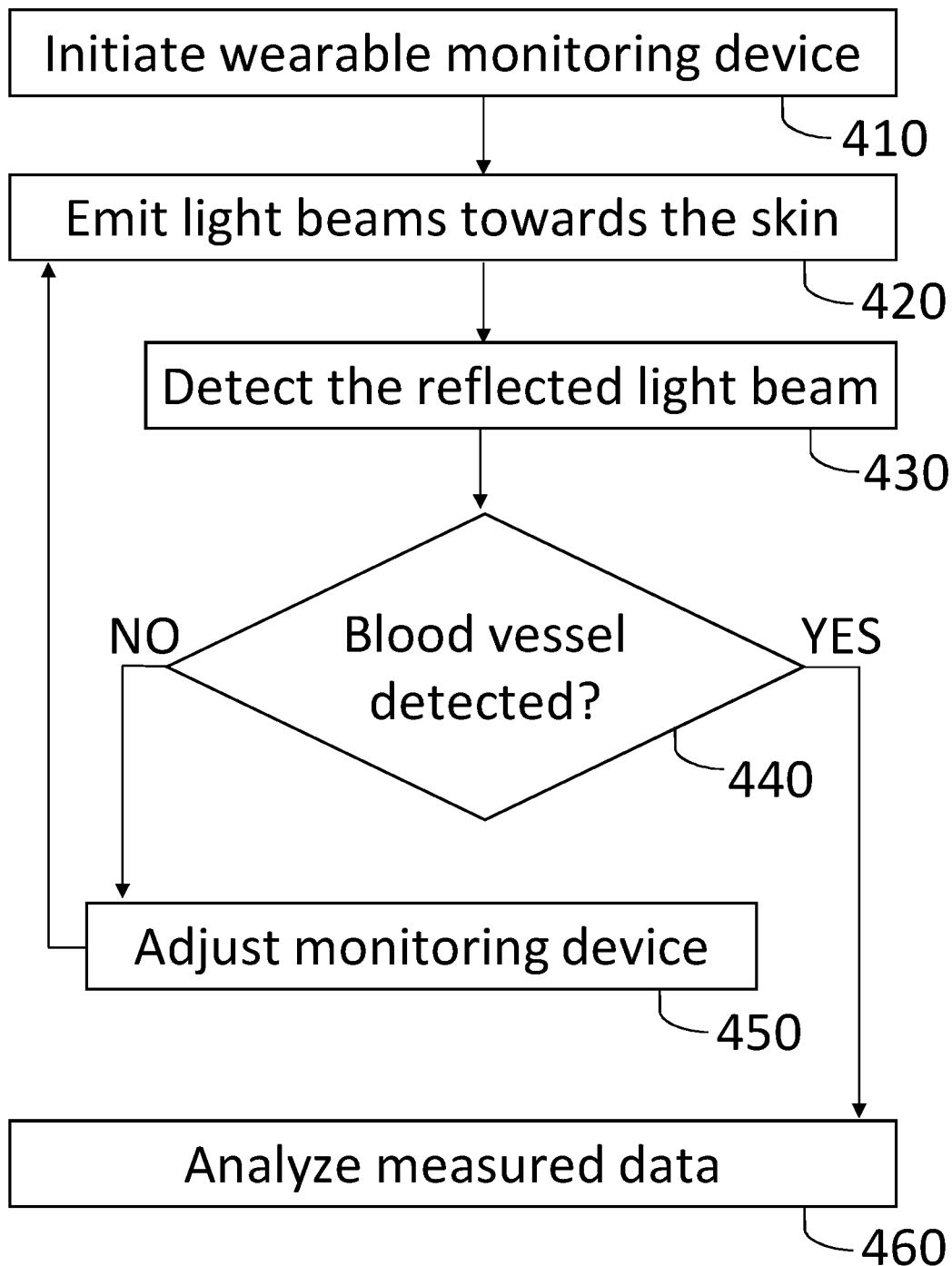
FIG. 4 shows a flowchart for a method of non-invasive monitoring of physiological measurements, according to some embodiments of the present invention.

Reference is now made to FIG. 4, which shows a flowchart of a method of non-invasive monitoring of physiological measurements. According to some embodiments, the wearable monitoring device 110 may be initiated 410 (e.g. by a processor of computerized device 120), for instance upon detecting contact (e.g. with a pressure sensor or any other element sensitive to contact and/or pressure) with the skin of the user (as described above), in order to commence the measurements.

According to some embodiments, at least one light emitting source 220 may emit light beams 420 in the direction of the skin of the user, to be reflected from a blood vessel (e.g., by the content of the blood vessel) and then received 430 by at least one sensor 210. In some embodiments, the light beams are transmitted through the tissue (including the blood vessels therein) of the user and then received by the sensor 210.

According to some embodiments, the wearable monitoring device 110 may be calibrated prior to initial use (as described above) such that the received light beams may provide an indication whether a blood vessel is detected 440, in order to filter measurements that were not carried out with proper positioning over a blood vessel. In case that the received signal does not provide an indication of a measurement from a blood vessel, the monitoring device may be adjusted 450 so as to better align the at least one light emitting source 220 with an adjacent blood vessel. In some embodiments, such adjustment 450 may be carried out by the user slightly moving the wearable monitoring device 110 along the skin, or alternatively carried out electrically by adjustment of the illumination angle of the light emitting sources 220 and/or selection of at least one light emitting source 220 that provides signals from a blood vessel. Once the wearable monitoring device 110 is properly adjusted 450, the at least one light emitting source 220 may emit light beams 420 again in order to commence a new measurement until a suitable blood vessel measurement is detected.

For example, if five light emitting sources 220 sequentially emit light beams towards the skin and the received signal indicates that only the first two are adjacent to a blood vessel (according to the light absorption and reflection from and/or transmission through blood vessels with respect to the absorption and reflection/transmission of tissue not including blood vessels), only information from these two light emitting sources 220 may be employed for the measurement.

According to some embodiments, in case that the received signal does not provide an indication of a measurement from a blood vessel, at least one of the light emitting sources 220 may be adjusted to emit light at a different wavelength. In some embodiments, if only some of the light emitting sources 220 are utilized to detect a blood vessel then at least one other light emitting source 220 (at a different position on the wearable monitoring device 110) may be utilized to emit light so as to detect a blood vessel from a different position of the light emitting source 220 (e.g. an LED) on the wearable monitoring device 110.

In some embodiments, if such adjustment of the measurement does not allow detection of a blood vessel, for instance after a predetermined number of periodic tests (e.g. five tests), then an alert may be provided to the user.

In case that the received signal provides an indication of a measurement from a blood vessel, the measured data may be analyzed 460 in order to monitor the physiological signals of the user. For example, analyzing the received data to check a change in glucose level, whereby such analyzing may be based on previous calibration (as described above).

In some embodiments, the analyzing 460 of the measurements may be carried out at a computerized device 120 and/or at a data analyzing facility 130 (as described with reference to FIG. 1).

Figure 5:
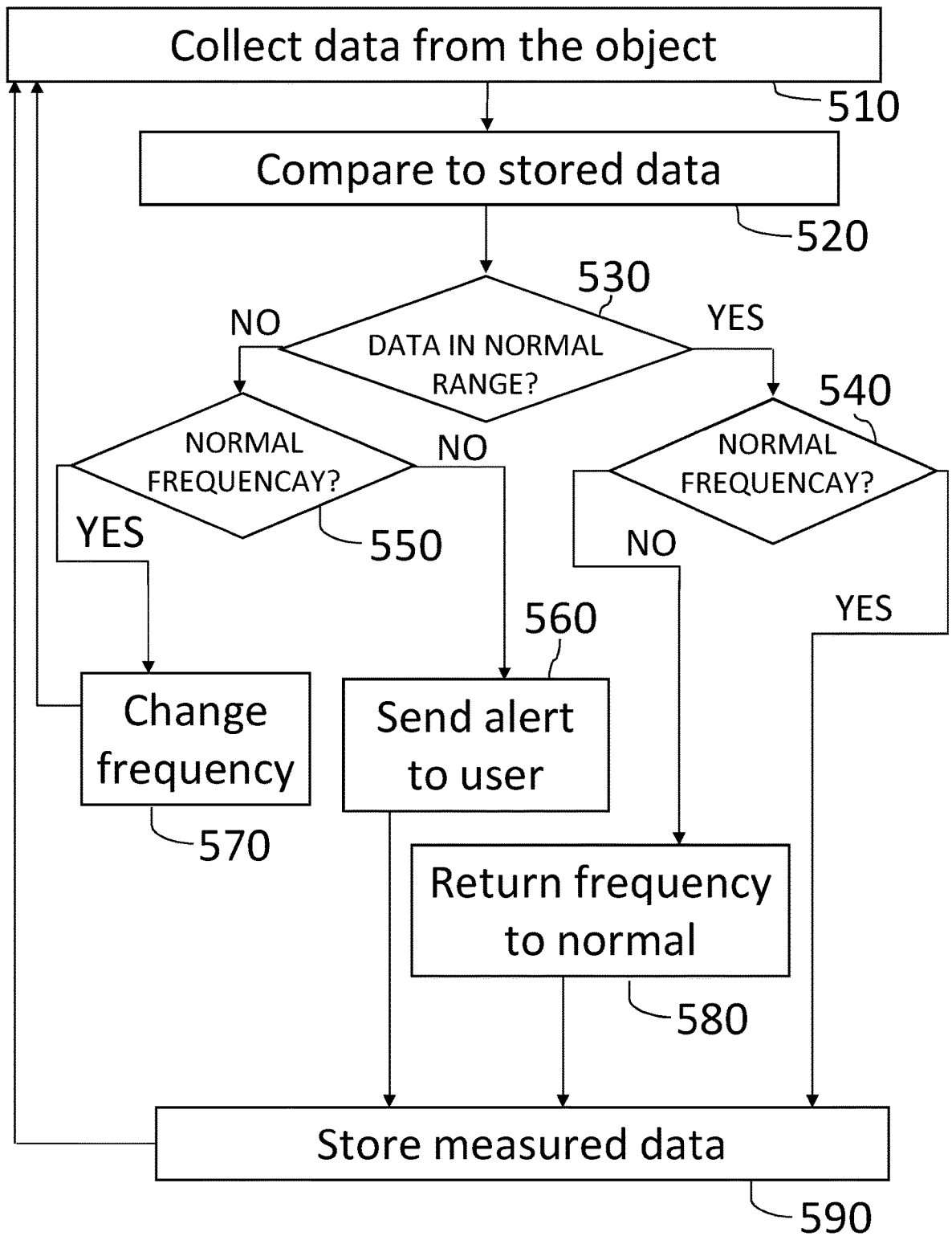
FIG. 5 shows a flowchart for a method of analyzing non-invasive monitoring of physiological measurements, according to some embodiment of the present invention.

Reference is now made to FIG. 5, which shows a flowchart of a method of monitoring and analyzing non-invasive physiological measurements. According to some embodiments, the analyzing 460 of the data measured by the wearable monitoring device 110 may be carried out to determine whether the physiological signals of the object 10 are within the desired range, for instance by calibrating physiological signals it may be possible to determine a desired range for the received signals and/or the desired range may correspond to data gathered from multiple subjects and/or the desired range may correspond to a specific range provided (e.g. by health officials) for particular substances in the blood.

After a blood vessel is detected 440, the measured data of the object 10 may be collected 510 for analyzing by the monitoring system 100. For instance, the measured data may be collected and stored in a dedicated memory unit embedded into the wearable monitoring device 110. The collected data may then be transferred to the computerized device 120 and/or the data analyzing facility 130 for further analyzing.

In some embodiments, the collected data may be compared 520 to at least one stored data set in order to determine whether the collected data is within a normal range 530. According to some embodiments, the stored data may be stored at a dedicated memory unit at the wearable monitoring device 110 and/or at the computerized device 120 with data from previous measurements of the object 10. For example, the collected data may be compared to a threshold value and/or the deviation from a threshold value may be calculated in order to compare the deviation to a desired deviation range.

After sufficient measurements of the object 10 are collected, for instance during calibration, a normal (or desired) range for the measurements may be determined, such that new measurements may be compared 520 to the normal range 530. For example, performing calibration for glucose measurements to establish a desired range for a particular object 10.

In some embodiments, the stored data for comparison includes average measurement data taken from measurements of the general public, whereby averaging values for a large group of people may provide a normal range for comparison.

According to some embodiments, the stored data may be used to improve the glucose level estimation accuracy, by comparing to stored temporal patterns within the optical measurements and corresponding glucose levels, and deriving low-dimensional representations of the corresponding optical measurements, best adhering to the glucose levels.

Moreover, the measured glucose levels may be used by the data analyzing facility 130 (e.g. cloud based), to apply statistical inference to the stored data of multiple users, in order to detect temporal patterns common to large numbers of users, and relating to physical activities.

In case that the collected data is within the desired range 530, the system may check if the frequency is at a normal (or predetermined) range 540. If the frequency is at a normal value 540 the measured data then may be stored 590 and aggregated for future measurements. If the frequency is not normal 540, then the system may return 580 the frequency to normal and also store 590 and aggregate the measured data for future measurements.

Otherwise, in case that the collected data is not within the desired range 530, the system may check if the frequency is at a normal (or predetermined) range 540. If the frequency is at a normal value 540 the system may change the frequency 570, for instance increasing the frequency of the measurements when a sharp rise (e.g. with a change of about 10-20% between measurement periods) in a physiological feature is detected, and then collect data 510 with the new measurement frequency.

If the frequency is not normal 540, then an alert may be sent 560 to the user (e.g. on a display) and also the collected data may be stored 590 for future reference together with collection of new measurement data 510 with the new measurement frequency. For example, a first measurement gives an indication that a measured glucose level is out of the desired range (i.e., lower or higher than predefined upper and lower limits) so the measurement frequency is increased and an alert is sent to the user. At the second measurement the glucose level is still out of the desired range, and at the third measurements the glucose level returns to normal range so that measurement frequency may be reduced to normal level. In some embodiments, an alert may also be created when the data return to the normal range.

For example, two computational tests are applied to the spectral measurements. In the first test, the dynamics of the glucose levels are compared to those computed using a low-dimensional embedding of the spectral measurements. It follows that the spectral measurements follows closely the dynamics and trends of the glucose levels. In particular, as the number of samples increases (as on the third day of experiments) the parameterization accuracy is improved. Thus, it follows that the parameterization accuracy can be improved by using more test subjects and also a larger database. With the number of optical measurements increasing, and also corresponding reference glucose measurements, more elaborate numerical models may be derived. Thus, improving the glucose readings accuracy. In particular, when a large dataset of such measurements is accumulated, data mining and statistical inference techniques may be applied.

According to some embodiments, each user may be associated with a personal reflectance coefficient during calibration of the system. Such a personal reflectance coefficient may provide personal calibration data regarding parameters that may influence optical readings and thereby allow personalization of the measurements, as further described hereinafter. It should be appreciated that since each user has unique physical conditions, each user may need their own personal adjustments for the optical readings. These adjustments may therefore enable setting a personal offset in relation to average values that are previously stored in the database.

It should be noted that Infra-Red (IR) reflection in the human body may be affected by various parameters. User dependent parameters may include parameters affecting the optical reflection, such as different hand and/or skin thickness, different skin complexions, thickness and diameter of blood vessels, and thickness and composition of different skin layers. Other user dependent parameters may affect (or alter) the results of the measurement, such as hair on the wrist, skin temperature, user activity level (e.g. causing sweating), and dehydration level.

Environmental dependent parameters may also affect the result, such as the amount of external light radiation combined with light beams of the measurement, the type of external light radiation, the angle and distance between the IR light source and the blood vessel, the diversity of IR light sources (e.g. additional IR light sources with a different wavelength), light source decay during operation, and possible water presence (e.g. in ambient air or on the body).

According to some embodiments, certain reference parameters in the blood cycle, that may be considered as constant, may be defined as a reference level for each user (e.g. during calibration). Thus, comparison to that reference level may indicate changes in the measured parameters of the individual user. It should be appreciated that since the values of these reference parameters may change in a relatively narrow range (and in a slow rate), these reference parameters may be utilized for calculation of the relevant personal reflectance coefficient for each user.

It should be noted that the personal reflectance coefficient may represent for each user reference parameters (being relatively constant) that influence light transmittance, reflectance and absorbance through tissue of the body. These reference parameters do not vary, since they correspond to skin, tissue and blood vessel structure that is a part of the optical path of which the light beams from the light source go in and are reflected, absorbed or transmitted back towards the detector, for example as shown in FIG. 3B.

In some embodiments, substantially constant bloodstream components (e.g. Albumin, serum proteins, globulins and any combination thereof) may be considered as a "mirror with known reflection index" reflecting back the light (e.g. IR light), through skin, blood and blood vessels, with a known (or constant) optical behavior. Such reference parameters (with known optical behavior) may be therefore defined for each user, for instance during calibration, such that reflectance, absorbance and transmittance of light during glucose measurements may be determined. For example, two possible blood parameters may be chosen as Albumin and $CO_2$ level dissolved in the blood (associated with blood vessels blueish color), which can be considered as constant with healthy users. Changes in such substantially constant parameters as Albumin may occur in healthy people, for instance during three weeks, in a narrow range of about 3.5-5 gr/dl. The amount of $CO_2$ dissolved in blood may stay constant as long as the user is not suffering from any serious distress or illness, so a change in dissolved $CO_2$ levels may therefore indicate a distress in a particular user.

It should be appreciated that since Albumin (or other constant parameter) values do not vary dramatically for each user, these values may be utilized to constantly recalculate the personal reflectance coefficient for each user. Thus, all varying parameters within the blood may be compensated for with the known value for Albumin (or other serum proteins), whereby the other parameters may be compared to a reference level for the known values. For instance if a user moves the device on the hand, the angle and distance between the light source and the blood vessel may change and therefore the optical reading may be different. Therefore it may be possible to calculate a compensation function based on changes in the Albumin (and/or other blood serum proteins) reading, so as to derive that the user moved the device, and thus applying the compensation function on reading of other parameters (e.g. of glucose), as further described in FIG. 6. In some embodiments, the base value of Albumin (and/or other blood serum proteins) for this user may be accordingly derived from previously acquired databases based on the cluster of data that this particular user belongs to, or from previous results of general blood test that are available at medical databases.

Figure 6:
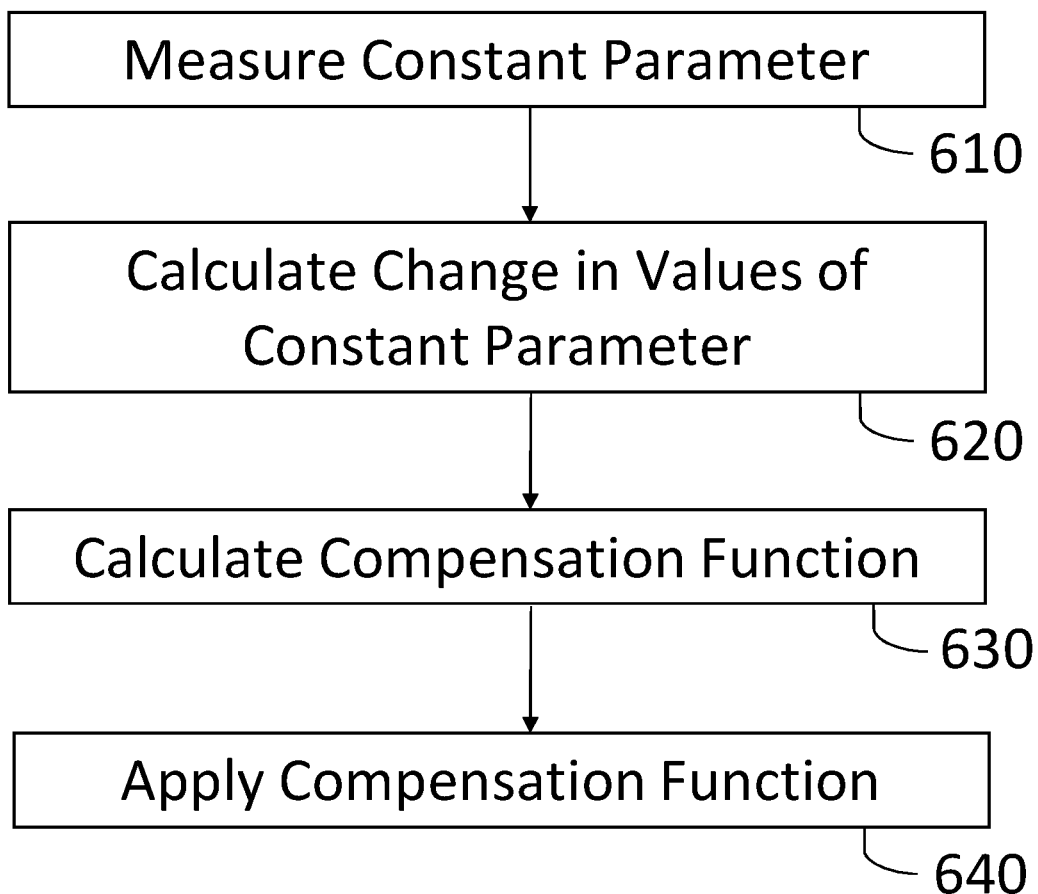
FIG. 6 shows a flowchart for a method of compensating blood parameter readings, according to some embodiment of the present invention.

Reference is now made to FIG. 6, which shows a flowchart of a method of compensating blood parameter readings, according to some embodiments. Initially, a measurement 610 may be carried out for a particular substantially constant parameter in the blood (such as Albumin). In some embodiments, a change may be calculated 620 (e.g. for Albumin) relative to a reference value for that parameter (e.g. Albumin), for instance reference value may be derived from a database of average values for populations having similar characteristics (e.g. for elderly women).

In some embodiments, the reference value may be derived from a reference conversion lookup table (e.g. initially created in laboratory conditions) associating an optical reading of a particular substance with the actual value. For example, having a sample of a known amount of Albumin (or glucose) in a known concentration (e.g. 4 gr/dl), that is irradiated with IR radiation in a known wavelength. Thus, future optical reading of the same (or similar) wavelength should be converted to the actual value of the measured parameter, e.g. Albumin or glucose, so as to allow pre usage calibration as well as future calibration after measurements. In some embodiments, an additional reference lookup table may also be provided (e.g. initially created in laboratory conditions) for tissues of different groups of patients, for instance provide a reference tissue of a Hispanic woman with a predefined skin color, that may be used to convert optical IR readings to actual values of the tissue.

Then, a compensation function may be calculated 630 based on the previously calculated change 620 in the constant parameter (e.g. Albumin) reading. Finally, the compensation function may be applied 640 on readings of other parameters (e.g. on glucose) in order to normalize the readings of those parameters. Thus, due to a known value of a particular reference parameter (e.g. Albumin), other parameters may be calibrated in order to provide a reading that is not affected by other factors. It should be noted that while Albumin is described herein, any other substantially constant parameter may be similarly calculated and applied for the calibration process. It should be further appreciated that more than one substantially constant parameter may be used.

Reference is now made to FIG. 7, which schematically illustrates a cross-sectional view of the measuring unit 700 with an embedded ultrasonic unit 720 coupled and adjacent to the subject (wherein the direction of the dashed arrows indicates the direction of the light beams), according to an embodiment of the present invention. According to some embodiments, monitoring of thickness of a user's skin tissue may be allowed with positioning of non-invasive monitoring system 100 above a blood vessel.

Measuring unit 700 may be placed adjacent to the skin 30 of the subject. A light beam may then be emitted from the light emitting source 220 and into the skin such that it penetrates the skin and may be reflected back from blood vessel 35 towards sensor 210. The difference in the data between the emitted beam and the received (reflected) beam may provide an indication on the radiation absorption by the blood in blood vessel 35 and thus may indicate characteristics and blood measurements of the blood inside blood vessel 35, in a non-invasive procedure. In some embodiments, measuring unit 700 may further include at least one ultrasonic unit 720 capable of transmitting and receiving ultrasound signals.

It may be appreciated that an ultrasonic transducer may include a set of crystals which may transmit and receive ultrasound signals derived from changes in their magnetic field. In some embodiments, an array of such crystals may be embedded into non-invasive monitoring system 100, for example embedded into measuring unit 700. The ultrasonic transducer may also turn these signals into electrical currents. Different ultrasonic signals may penetrate and propagate through skin tissue, and may be reflected back to the transducer depending among other parameters on the operational frequency, and/or on tissue water content, and/or on tissue density. In some embodiments, signals of reflected ultrasound waves may be separated according to the depth of tissue from where these waves are reflected from. In some embodiments, a set of piezo crystals arranged in a predetermined pattern may be used for continuously measuring the skin thickness above blood vessels, for example in the lower part of the wrist, and thereby determine the position of a transducer and/or its proximity to blood vessels.

In some embodiments, such a set of crystals may be positioned such that in predetermined time periods and/or every time the monitoring device is removed and/or replaced, the set of crystals may transmit and receive ultrasonic signals through the skin. These signals may determine skin tissue thickness underneath the transducers array and/or determine transducer array proximity to blood vessels under the measured skin.

In some embodiments, determination of desired parameters from monitoring of signals reflected from blood vessels, for instance using non-invasive monitoring system 100, may be accomplished with at least one of predefined arrangement of crystals, and/or predefined distance between them, and/or predefined frequency.

In some embodiments, the signal to noise ratio, for instance with non-invasive monitoring system 100 for glucose measurements, with IR signals reflected from human tissue, may be at a ratio of 150 to 1, where sources of noise may be for example background lighting.

Figure 8A:
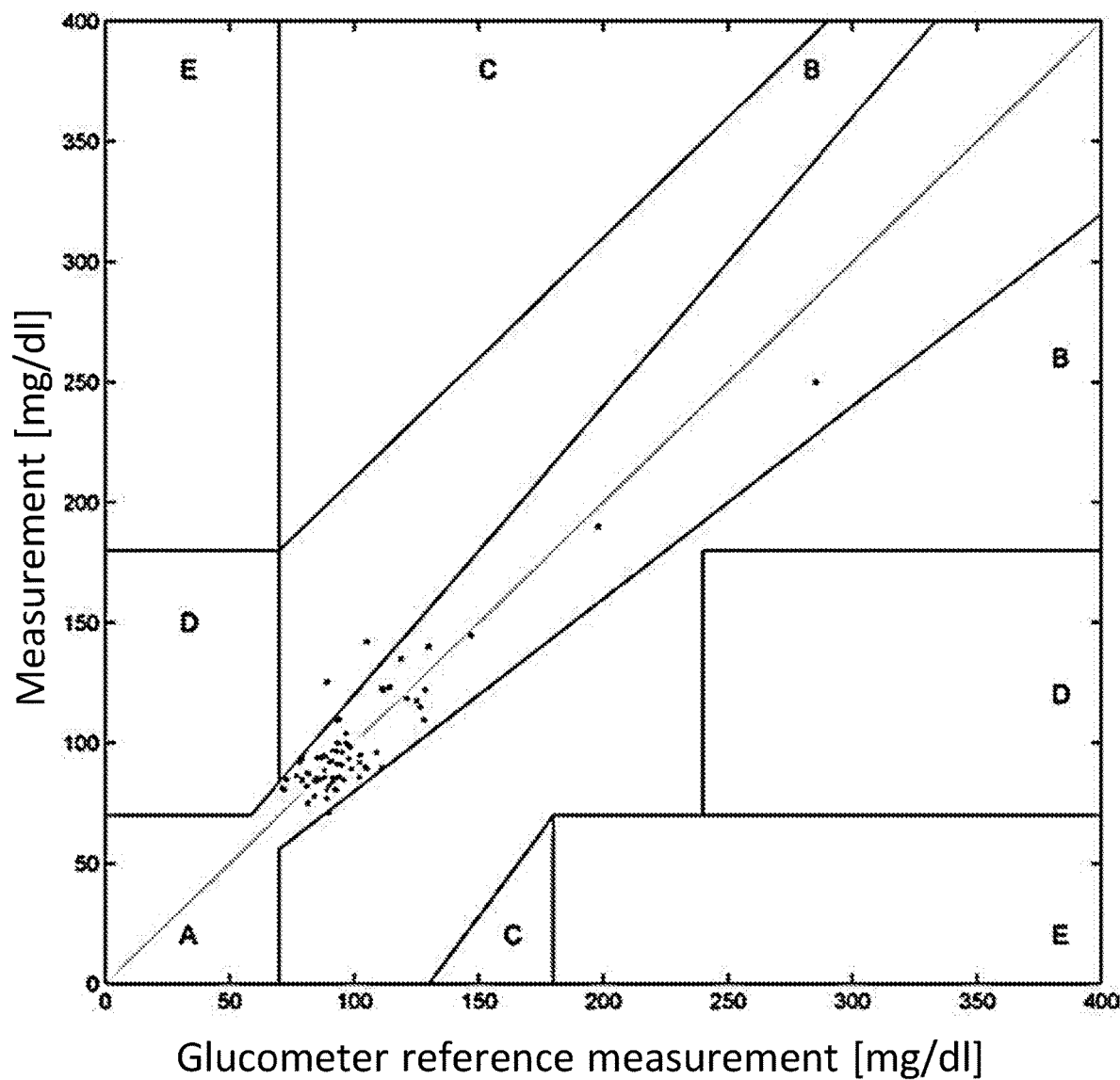
FIG. 8A shows a Clarke Error Grid chart for a first measurement with a non-invasive monitoring system, according to some embodiments of the present invention.
Figure 8B:
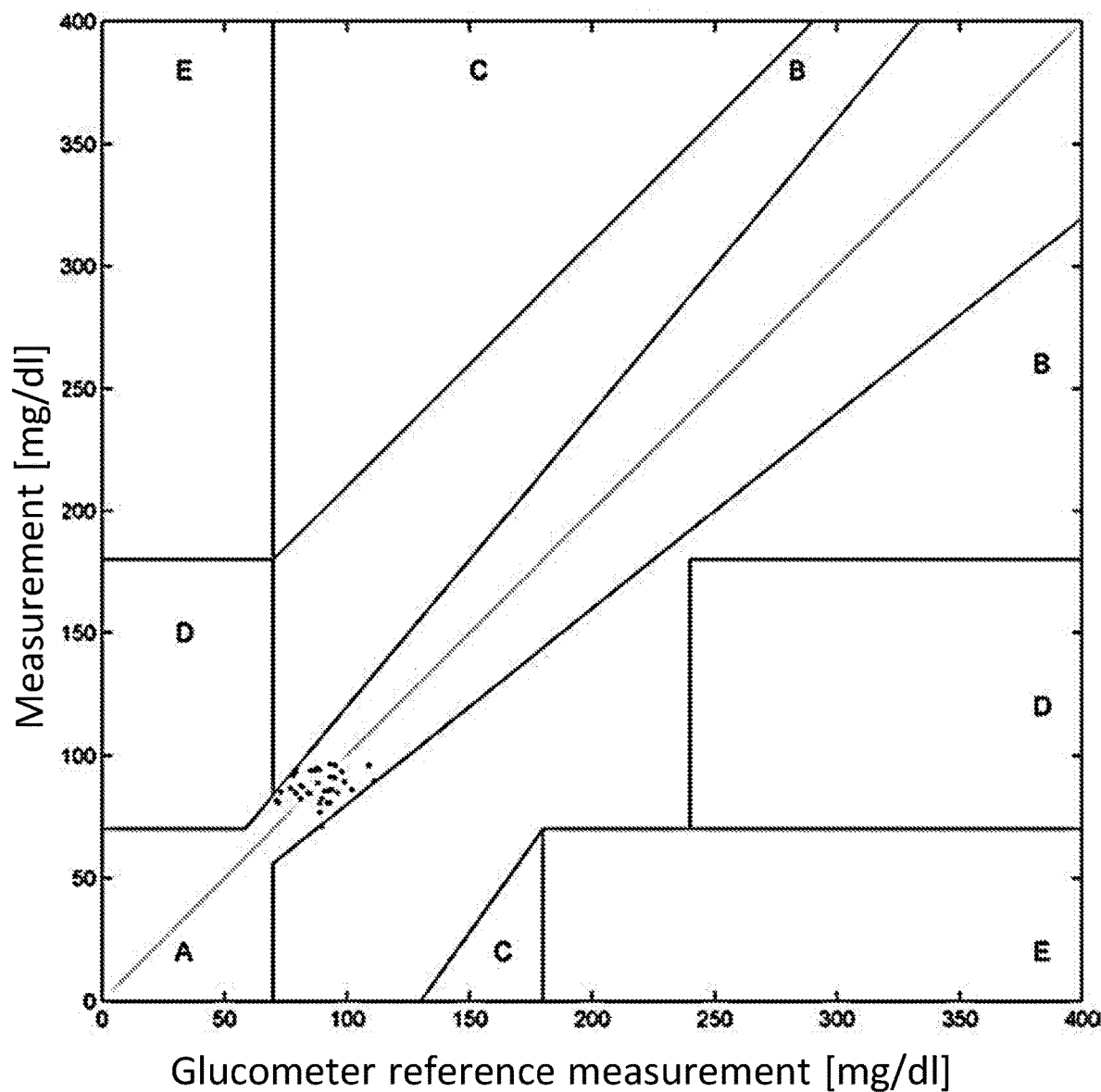
FIG. 8B shows a Clarke Error Grid chart for a second measurement with a non-invasive monitoring system, according to some embodiments of the present invention.

Reference is now made to FIGS. 8A-8B, which show a Clarke Error Grid chart for a first and a second measurement with non-invasive monitoring system 100. A test has been initially conducted for monitoring of glucose for a test group of eight users receiving 50 grams of glucose after fasting for ten hours. The monitoring have been measured for about 4-6 hours about every 30 minutes, wherein non-invasive monitoring system 100 has been compared to monitoring with commercially available invasive glucometers (e.g. "Accu-Check"™) as reference for a given blood test. The results of this test are shown in FIG. 8A with a Clarke Error Grid (CEG), where compatibility of over 96 percent has been observed in zone "A" for measurements with non-invasive monitoring system compared to FDA approved glucometers.

In a second test experiment, monitoring of glucose for a test group of eight users has been conducted, wherein each member of the test group received about 2000 milligrams of a pain relieving medication containing Acetaminophen (e.g. administered with a pill of "Acamol"™), after users of the test group have been fasting for ten hours. It may be appreciated that Acetaminophen exhibits a unique spectral signal with optical measurements, and therefore can be detected with non-invasive monitoring system 100. The results of this test are shown in FIG. 8B with a Clarke Error Grid (CEG), where compatibility of over 97 percent has been observed in zone "A" for measurements with non-invasive monitoring system compared to FDA approved glucometers.

It may be appreciated, for instance from a Clarke Error Grid chart in FIG. 8B, that using the monitoring device, as described above, glucose monitoring may not be affected by presence of Acetaminophen since the optical properties of glucose in the blood may not be affected by the presence of Acetaminophen, for example in contrast to reading by a commercially available continuous glucose monitoring (CGM, for example such as "Dexcom platinum G4") which is sensitive to Acetaminophen presence in the blood.

In some embodiments, the amount of Acetaminophen may be monitored and/or measured, due to the unique spectral signal of Acetaminophen, so as to serve as a monitoring unit for acetaminophen, where such measurement may allow determination of accurate reading of other substances in the blood, for instance glucose. Therefore, monitoring, for instance with non-invasive monitoring system 100, may be carried out even with users receiving medications and still provide substantially accurate monitoring thereby enhancing compliance of monitoring with various medications.

Figure 9A:
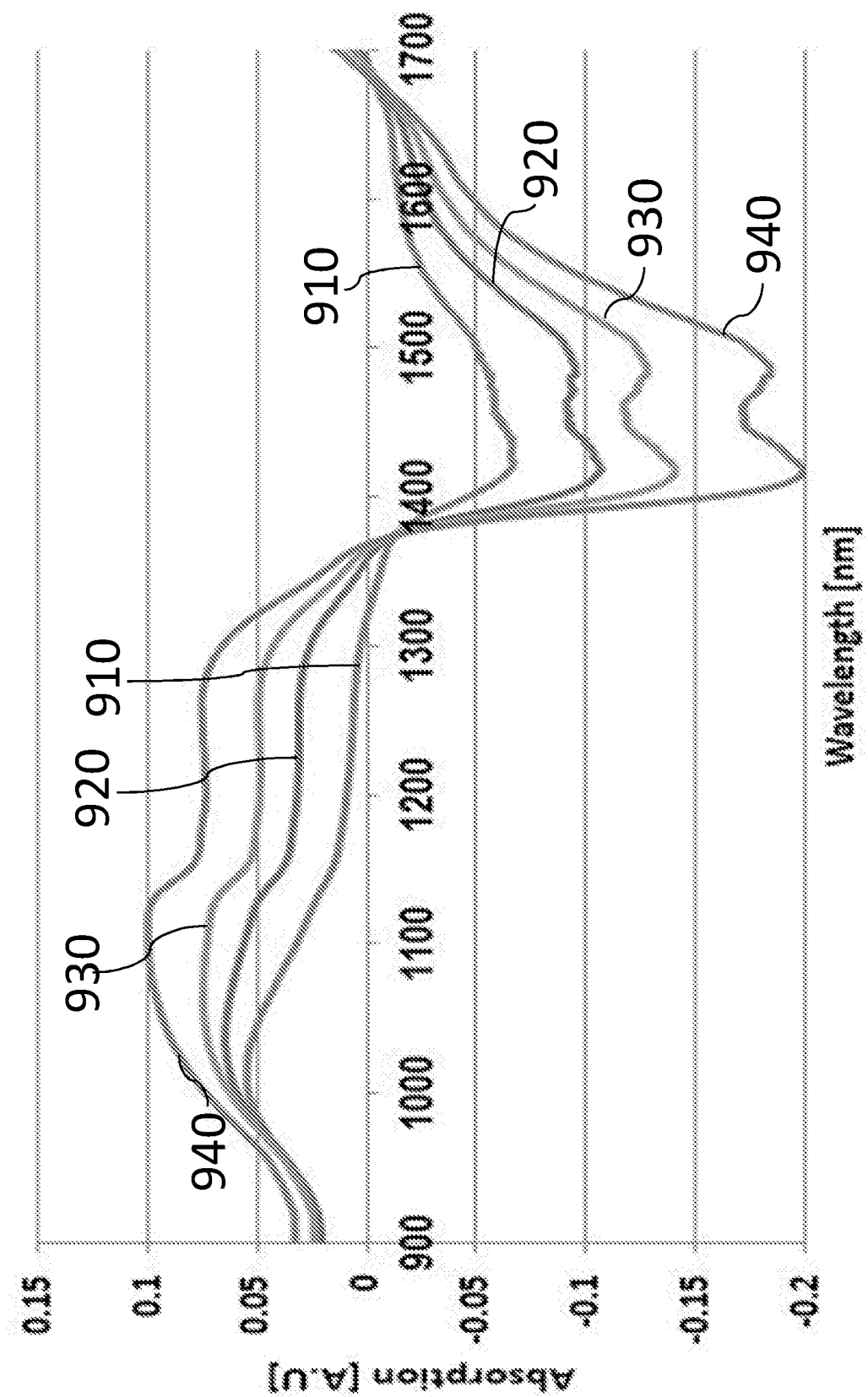
FIG. 9A shows absorption measurements with a non-invasive monitoring system for Albumin, according to some embodiments of the present invention.
Figure 9B:
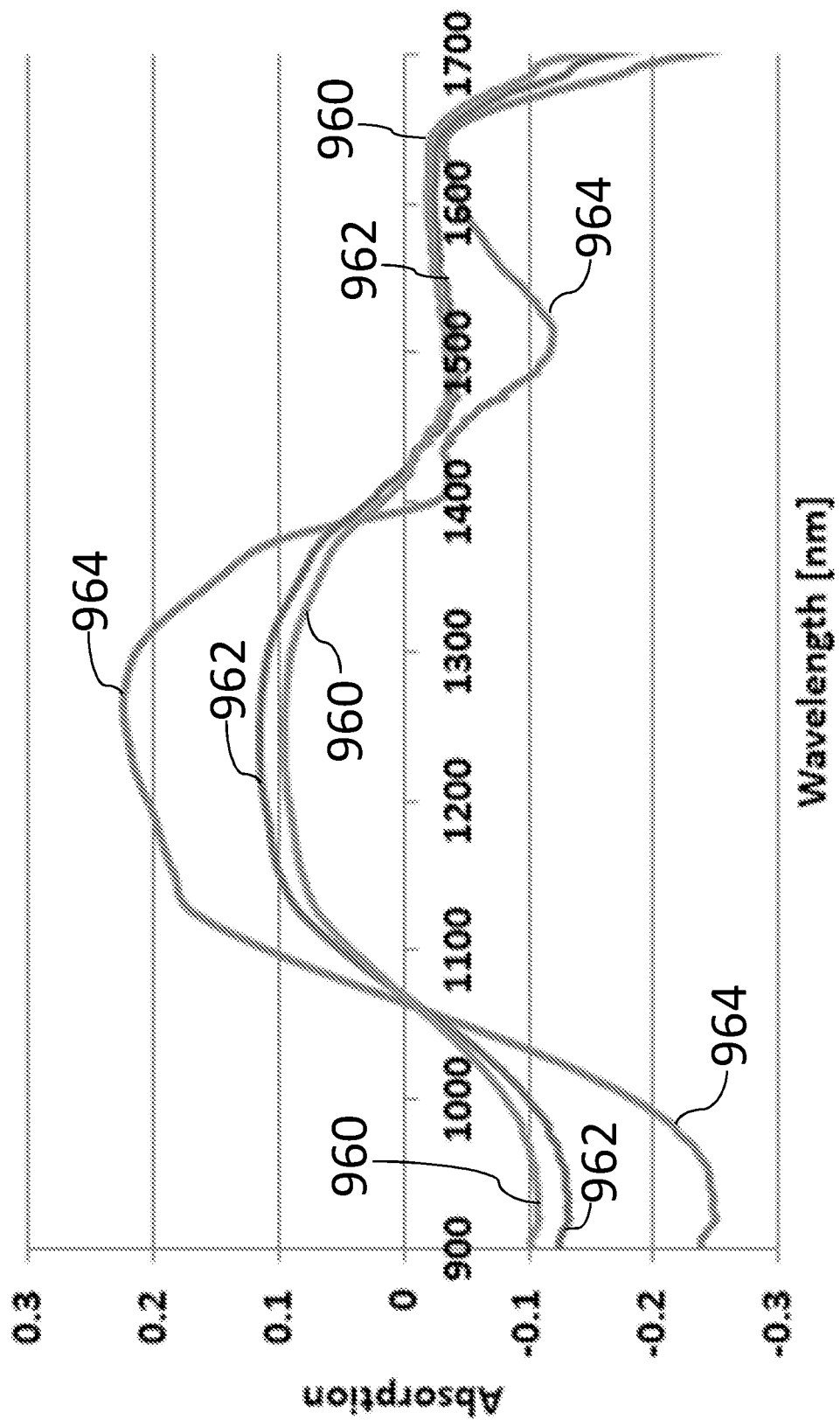
FIG. 9B shows absorption measurements with a non-invasive monitoring system for low density lipoprotein (LDL), according to some embodiments of the present invention.
Figure 9C:
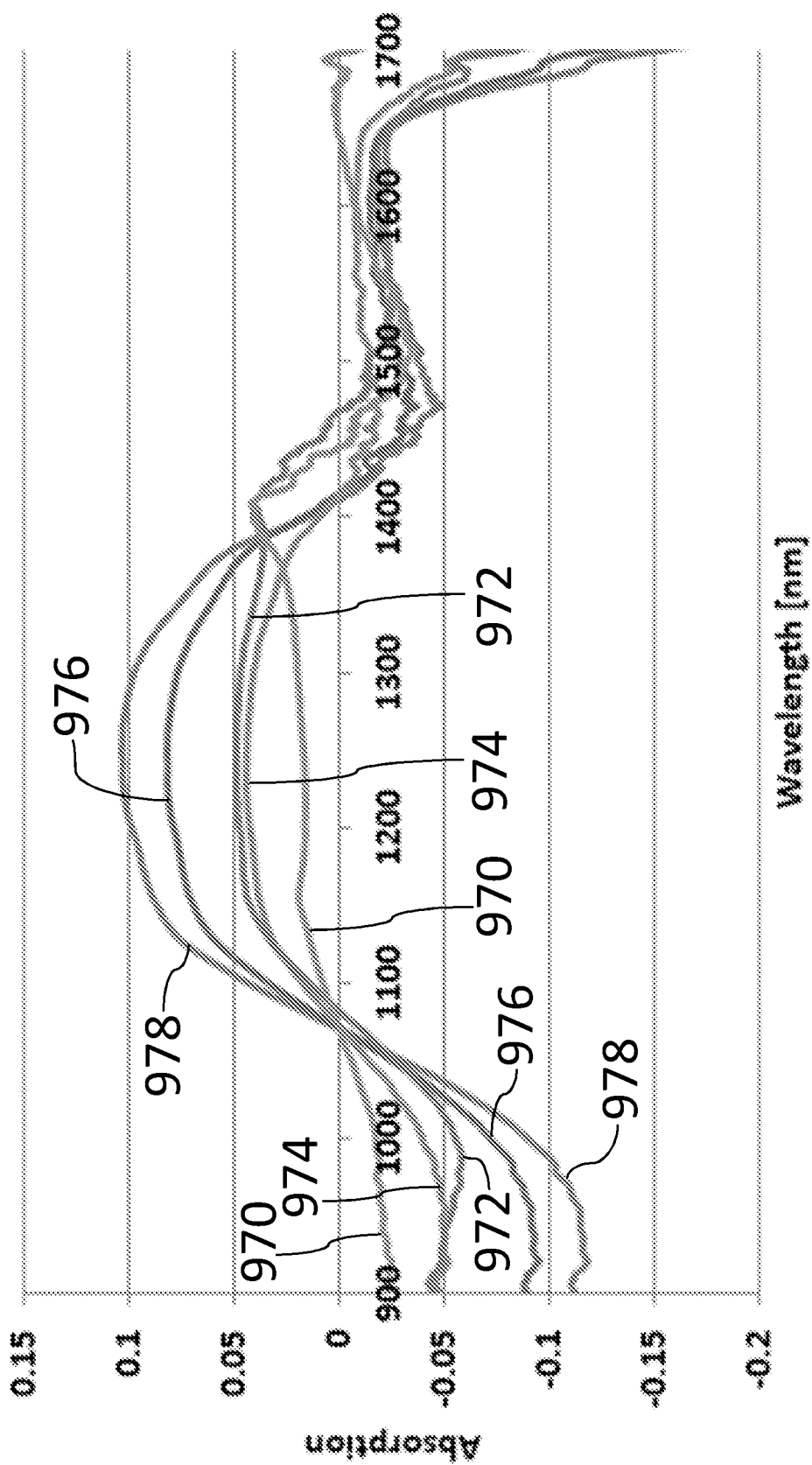
FIG. 9C shows absorption measurements with a non-invasive monitoring system for very low density lipoprotein (vLDL), according to some embodiments of the present invention.

Reference is now made to FIGS. 9A-9C, which show absorption measurements with non-invasive monitoring system 100, for Albumin, LDL and vLDL respectively. It should be noted that these absorption measurements with non-invasive monitoring system 100, as shown in FIGS. 9A-9C, are carried out on predetermined samples with known concentrations (e.g., with test tubes containing blood sample with known Albumin concentration) so that they may be used for calibration of absorption values.

A test has been conducted for Albumin absorption, as shown in FIG. 9A, for four different concentrations of Albumin in blood. Line 910 indicates concentration of ~1 g/dL, line 920 indicates concentration of ~3 g/dL, line 930 indicates concentration of ~5 g/dL, line 940 indicates concentration of ~10 g/dL for Albumin.

A test has been conducted for LDL absorption, as shown in FIG. 9B. Line 960 indicates measurements with concentration of ~500 microgram/milliliter, line 962 indicates measurements with concentration of ~700 microgram/milliliter, and line 964 indicates measurements with concentration of ~1200 microgram/milliliter.

A test has been conducted for vLDL absorption, as shown in FIG. 9C. Line 970 indicates measurements with concentration of ~50 microgram/milliliter, line 972 indicates measurements with concentration of ~100 microgram/milliliter, line 974 indicates measurements with concentration of ~150 microgram/milliliter, line 976 indicates measurements with concentration of ~250 microgram/milliliter, and line 978 indicates measurements with concentration of ~300 microgram/milliliter.

As may be appreciated by one of ordinary skill in the art, FIGS. 9A-9C show that there is a direct correlation between the concentration and the absorption values, where changes between positive and negative peaks indicate different wavelength bands (as the scale can be normalized for each test). With such measurements on samples with known concentration values, each absorption value (e.g., at a peak for a specific wavelength) may be correlated to the corresponding concentration of the substance. Thus, future measurements with non-invasive monitoring system 100 on a subject indicating a particular absorption value (e.g., for LDL) may be correlated to the corresponding concentration of that substance in the blood of the subject.

Unless explicitly stated, the method embodiments described herein are not constrained to a particular order in time or chronological sequence. Additionally, some of the described method elements may be skipped, or they may be repeated, during a sequence of operations of a method.

Various embodiments have been presented. Each of these embodiments may of course include features from other embodiments presented, and embodiments not specifically described may include various features described herein.

The invention claimed is:

1. A monitoring device configured as a wearable band and adapted to be in contact with a tissue of a subject's body, the device comprising:
    a measuring unit, comprising:
        at least two light emitting sources configured to illuminate tissue adjacent to the light sources; and
        a plurality of sensors configured to detect, at different positions along the tissue, radiation that is transmitted through the tissue and is reflected back from blood vessels in the tissue and from the content of the blood vessels as a result of the illumination emitted from the at least two light emitting sources;
    wherein the measuring unit is configured to measure the detected radiation, and
    a controller, coupled to the measuring unit and receiving measurements therefrom, and configured to:
    drive the at least two light emitting sources to emit the illumination;
    derive from the measurements at least one absorption measurement of at least one respective component in the blood that comprises at least one of: albumin and triglycerides,
    associating a plurality of personal reflectance coefficients derived from the at least one absorption measurement with a corresponding plurality of subjects,
    analyze, from the measurements, a concentration of glucose in the blood of the subject; wherein the analysis is personalized, based on the personal reflectance coefficients and adjusted with respect thereto, and
    issue an alert when the concentration of glucose in the blood exceeds a predetermined threshold,
    wherein the device is configured as a wearable band that is adapted to be in contact with the tissue of the subject's body and is further configured to indicate the concentrations with respect to the personal reflectance coefficients.

2. The device of claim 1, wherein the illumination emitted from the at least two light emitting sources at a first sampling frequency is used for a first measured physiological characteristic, and the illumination emitted from the at least two light emitting sources at a second sampling frequency is used for a second measured physiological characteristic.

3. The device of claim 1, wherein the at least one sensor is a light sensor configured to detect radiation reflected from a subcutaneous tissue of the subject, and wherein the sensors are configured to detect the reflected radiation in the infrared or near infrared spectrum.

4. The device of claim 1, wherein at least one light emitting source of the at least two light emitting sources operates at a different wavelength than at least another light emitting source of the at least two light emitting sources.

5. The device of claim 1, wherein the controller is further configured to control each light emitting source to emit the illumination in predetermined time intervals which are controllable by at least one of: the controller and the user.

6. The device of claim 1, wherein at least one of the light emitting sources is a polarized light source configured to emit the illumination with a predetermined polarization, and wherein at least one of the at least one sensor is a polarized light sensor configured to detect reflection of the polarized illumination, wherein the polarized sensor has a different polarization than the polarized light source.

7. The device of claim 1, further comprising a communication module, configured to allow communication with an external computerized device.

8. The device of claim 1, further comprising a pressure sensor configured to indicate excessive pressure on the skin of the subject.

9. The monitoring device of claim 1, wherein the controller is further configured to calibrate intensities of the reflected radiation with respect to a corresponding one of the at least two light sources.

10. The monitoring device of claim 1, wherein the controller is further configured to derive from the reflected radiation an indication that a position of the monitoring device on the tissue of the subject is proximal to a blood vessel, and initiate further measurements thereupon.

11. The monitoring device of claim 1, further comprising at least one positioning correction indicator configured to provide positioning improvements based on the derived personal reflectance coefficients.

12. A system for non-invasive monitoring of physiological measurements of a tissue of a subject's body, the system comprising:
    at least one monitoring device according to claim 1,
    wherein the at least one controller of the at least one monitoring device is implemented as a computerized device.

13. The system of claim 12, further comprising a data analyzing facility, in communication with the computerized device, the data analyzing facility configured to analyze measured physiological signals for at least one subject.

14. The system of claim 12, wherein the measuring unit further comprises an ultrasound unit configured to determine skin tissue thickness.

15. The system of claim 12, further comprising an acoustic sensor configured to provide acoustic data to the computerized device to be combined with optical data from the light emitting sources.

16. The system of claim 12, wherein the computerized device is further configured to calibrate intensities of the reflected radiation with respect to a corresponding one of the at least two light sources.

17. The system of claim 12, wherein the computerized device is further configured to derive from the reflected radiation an indication that a position of the at least one monitoring device on the tissue of the subject that is proximal to a blood vessel, and initiate further measurements thereupon.

18. A method of personalized non-invasive monitoring of components in the blood of a subject, the method comprising:
- illuminating a tissue of a subject's body using at least two light sources that are adjacent to the tissue;
- detecting, at different positions along the tissue, radiation that is transmitted through the tissue and is reflected back from blood vessels in the tissue and from the content of the blood vessels as a result of the illumination emitted from the at least two light emitting sources,
- measuring the detected radiation,
- deriving from the measurements at least one absorption measurement of at least one respective component in the blood that comprises at least one of: albumin and triglycerides,
- associating a plurality of personal reflectance coefficients derived from the at least one absorption measurement with a corresponding plurality of subjects,
- analyzing, from the measurements, a level of glucose in the blood of the subject, wherein the analysis is personalized, based on the personal reflectance coefficients and adjusted with respect thereto;
- indicating the concentrations with respect to the personal reflectance coefficients, and
- issuing an alert upon detection of the concentration of glucose in the blood exceeding a predetermined threshold.

19. The method of claim 18, further comprising comparing two consecutive measurements to detect a change.

20. The method of claim 18, further comprising calibrating intensities of the at least two light sources.

21. The method of claim 18, further comprising receiving an indication on position on the skin of the subject that is proximal to a blood vessel.

22. The method of claim 18, further comprising:
- comparing data concerning an illumination intensity to an intensity of the detected radiation; and
- providing an indication on radiation absorption by the blood based on the comparison.

23. The method of claim 18, further comprising directing component of the illumination in predefined directions.

24. The method of claim 18, wherein the detecting, the measuring, the deriving and the analyzing are initiated upon detection of contact with the skin of the subject.

25. The method of claim 18, further comprising:
- checking if the measurements are within a predetermined range; and
- issuing an alert if the measurements are outside the predetermined range.

26. The method of claim 18, further comprising grouping users by the derived personal reflectance coefficients.

27. A wearable monitoring device comprising:
- a measurement unit comprising a plurality of light emitting sources and a plurality of sensors, the measurement unit configured to illuminate a tissue to which the device is attached and measure, at different positions along the tissue, reflected radiation from blood vessels and their content within the tissue, and
- a processing unit configured to derive from the measurements:
  - reference levels for each user of specified reference parameters,
  - personal reflectance coefficients, and
  - concentrations of albumin, triglycerides and glucose in the blood from respective absorption measurements thereof,
wherein the device is configured as a wearable band that is adapted to be removably attachable to the tissue of the subject's body, and is further configured to indicate the concentrations with respect to the personal reflectance coefficients.

28. The wearable monitoring device of claim 27, wherein at least some of the light emitting sources and the sensors operate in at least one of: the infrared and the near infrared ranges.

29. The wearable monitoring device of claim 27, wherein the light emitting sources and the sensors are coordinated temporally.

* * * * *

UNITED STATES PATENT AND TRADEMARK OFFICE
CERTIFICATE OF CORRECTION

PATENT NO. : 11,129,556 B2
APPLICATION NO. : 16/065817
DATED : September 28, 2021
INVENTOR(S) : Bashan et al.

It is certified that error appears in the above-identified patent and that said Letters Patent is hereby corrected as shown below:

On the Title Page

At item (72), add inventor:
Giora Bar-Sakai, Tel Aviv (IL)

Signed and Sealed this
Fifth Day of April, 2022

Drew Hirshfeld
*Performing the Functions and Duties of the
Under Secretary of Commerce for Intellectual Property and
Director of the United States Patent and Trademark Office*